United States Patent
Zhao

(10) Patent No.: US 9,458,123 B2
(45) Date of Patent: Oct. 4, 2016

(54) METHODS, PHARMACEUTICAL COMPOSITIONS, THERAPEUTIC SYSTEMS, AND COMPOUNDS FOR TREATING B CELL MALIGNANCIES

(71) Applicant: Jiyong Zhao, Rochester, NY (US)

(72) Inventor: Jiyong Zhao, Rochester, NY (US)

(73) Assignee: University of Rochester, Rochester, NY (US)

( * ) Notice: Subject to any disclaimer, the term of this patent is extended or adjusted under 35 U.S.C. 154(b) by 19 days.

(21) Appl. No.: 14/378,082

(22) PCT Filed: Feb. 15, 2013

(86) PCT No.: PCT/US2013/026330
§ 371 (c)(1),
(2) Date: Aug. 11, 2014

(87) PCT Pub. No.: WO2013/123320
PCT Pub. Date: Aug. 22, 2013

(65) Prior Publication Data
US 2015/0010643 A1    Jan. 8, 2015

Related U.S. Application Data

(60) Provisional application No. 61/599,142, filed on Feb. 15, 2012.

(51) Int. Cl.
*C07D 307/71* (2006.01)
*A61K 45/06* (2006.01)
*A61K 31/345* (2006.01)

(52) U.S. Cl.
CPC ........... *C07D 307/71* (2013.01); *A61K 31/345* (2013.01); *A61K 45/06* (2013.01)

(58) Field of Classification Search
None
See application file for complete search history.

(56) References Cited

U.S. PATENT DOCUMENTS

| 3,330,724 A | 7/1967 | Van Essen et al. |
| 2002/0173524 A1 | 11/2002 | Collins et al. |
| 2009/0018123 A1 | 1/2009 | Sindkhedkar et al. |
| 2009/0118135 A1 | 5/2009 | Reed et al. |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface).*
Gibson "B-cell diversity decreases in old age and is correlated with poor health status," Aging Cell (2009) 8, pp. 18-25.*
Jordan, V. C. (Nature Reviews: Drug Discovery, 2, 2003, 205-213).*
PCT International Search Report and Written Opinion for PCT/US2013/026330, mailed Apr. 11, 2013.

* cited by examiner

*Primary Examiner* — Jeffrey S Lundgren
*Assistant Examiner* — William Lee
(74) *Attorney, Agent, or Firm* — LeClairRyan, a Professional Corporation

(57) ABSTRACT

This invention relates to a method of treating B cell malignancies, which involves administering to a subject a compound having a structure of formula (I) to cause cell death of a B cell malignancy, thereby treating the B cell malignancy in the subject. Also disclosed are a method of causing cell death of malignant B cells, pharmaceutical compositions and therapeutic systems comprising a compound having a structure of formula (I), and a compound having a structure of formula (I).

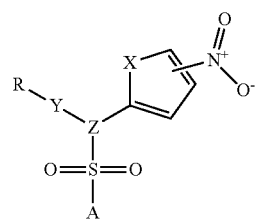

(I)

5 Claims, 15 Drawing Sheets

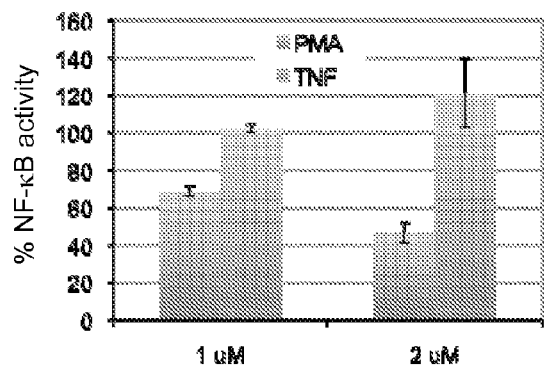
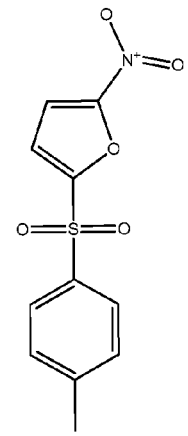
FIG. 1B                FIG. 1A
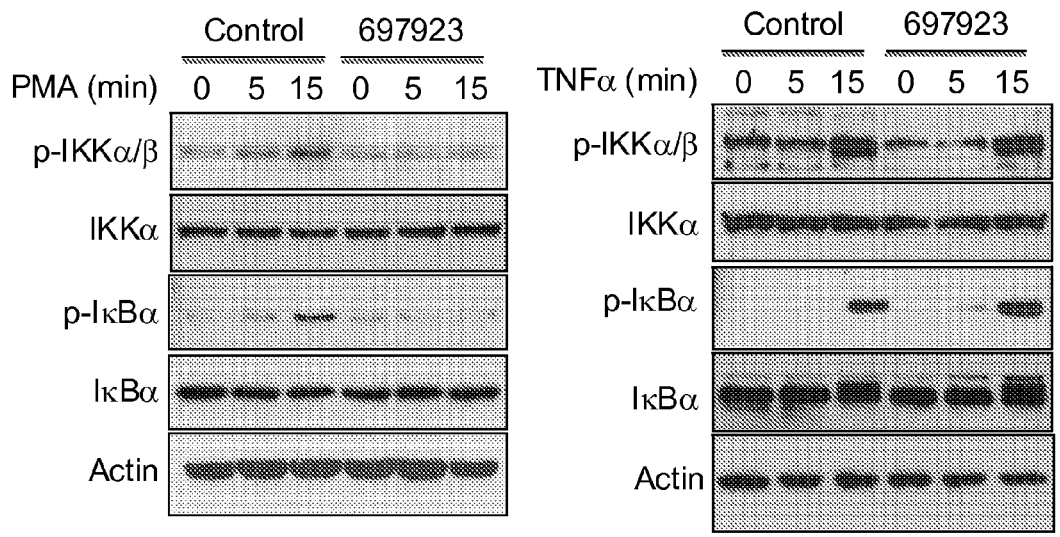
FIG. 1C

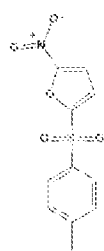 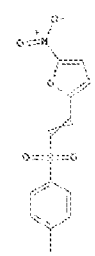 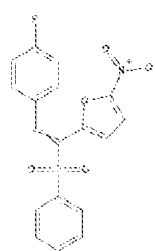
NSC697923    NSC291068    NSC291057
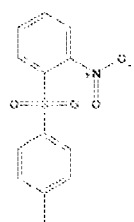 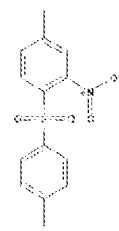 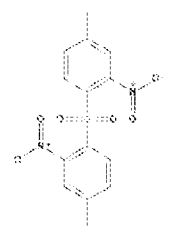
NSC627708    NSC646124    NSC656835
*FIG. 2A*
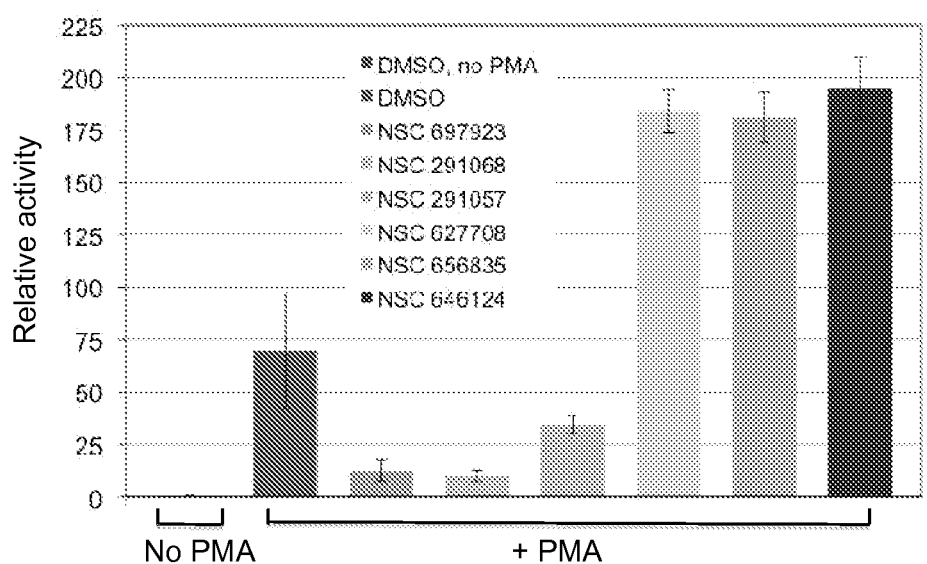
*FIG. 2B*

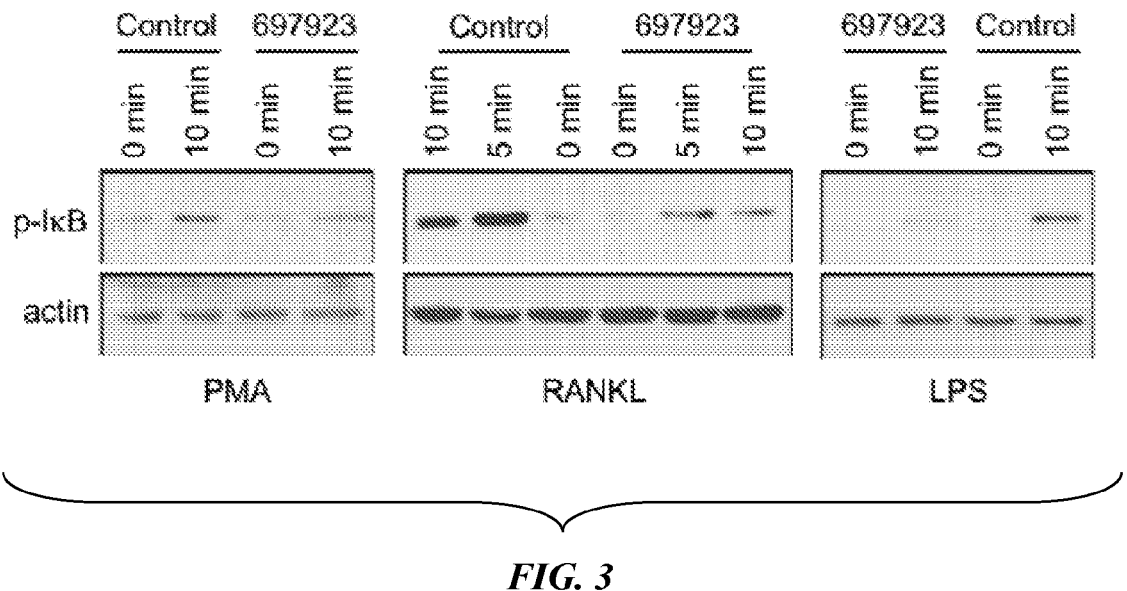
FIG. 3
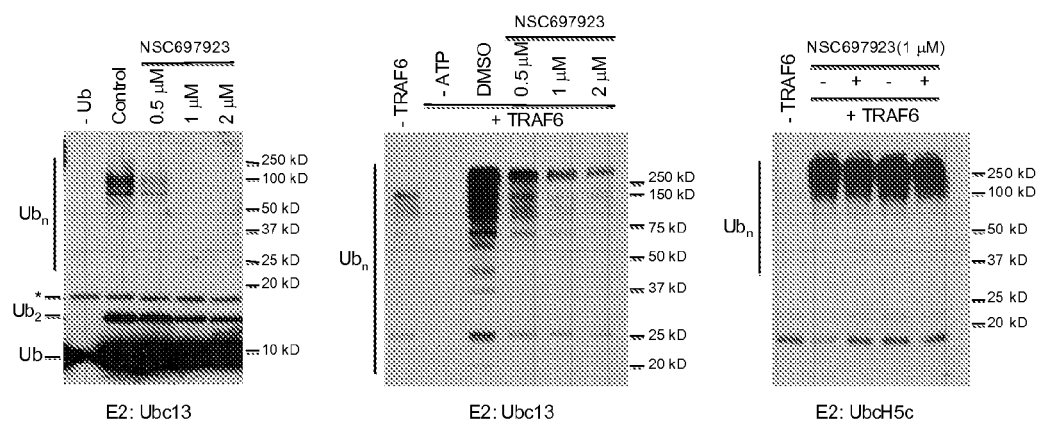
FIG. 4A  FIG. 4B  FIG. 4C

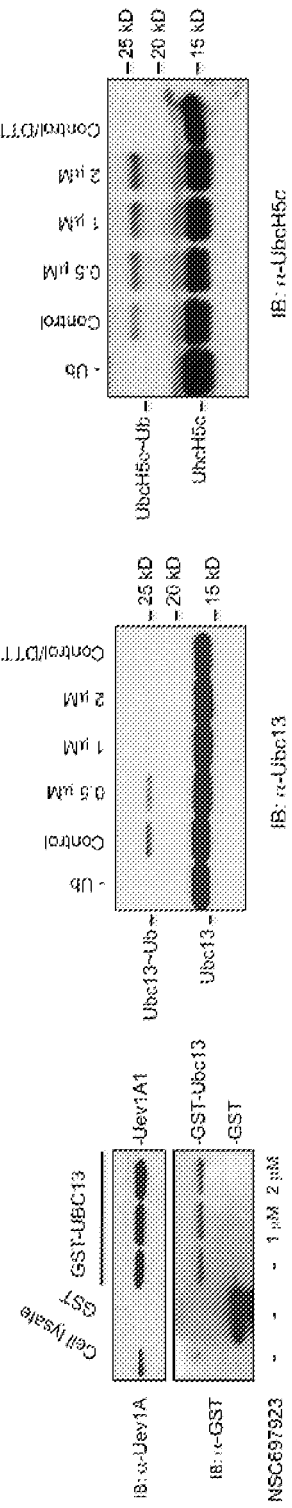

METHODS, PHARMACEUTICAL COMPOSITIONS, THERAPEUTIC SYSTEMS, AND COMPOUNDS FOR TREATING B CELL MALIGNANCIES

This application is a national stage application under 35 U.S.C. 371 from PCT Application No. PCT/US2013/026330, filed Feb. 15, 2013, which claims the priority benefit of U.S. Provisional Patent Application Ser. No. 61/599,142, filed Feb. 15, 2012, which is hereby incorporated by reference in its entirety.

FIELD OF THE INVENTION

This invention relates to methods, pharmaceutical compositions, therapeutic systems, and compounds for treating B cell malignancies.

BACKGROUND OF THE INVENTION

Diffuse Large B-Cell Lymphoma ("DLBCL") is an aggressive and heterogeneous disease comprising at least three major subtypes with distinct molecular, biological, and clinical properties: activated B-cell-like ("ABC") DLBCL, germinal center B-cell-like ("GCB") DLBCL, and primary mediastinal B-cell lymphoma ("PMBL") (Alizadeh et al., "Distinct Types of Diffuse Large B-cell Lymphoma Identified by Gene Expression Profiling," *Nature* 403:503-511 (2000); Lenz et al., "Aggressive Lymphomas," *N. Engl. J. Med.* 362:1417-1429 (2010); and Wright et al., "A Gene Expression-Based Method to Diagnose Clinically Distinct Subgroups of Diffuse Large B Cell Lymphoma," *Proc. Nat. Acad. Sci. U.S.A.* 100:9991-9996 (2003)). Although the overall cure rate for DLBCL reaches over 50% with the current therapies, such as R-CHOP, fewer than 40% of ABC DLBCL patients are cured (Friedberg et al., "Diffuse Large B-Cell Lymphoma," *Hematol. Oncol. Clin. North Am.* 22:941-952 (2008); Lenz et al., "Aggressive Lymphomas," *N. Engl. J. Med.* 362:1417-1429 (2010); and Staudt et al., "The Biology of Human Lymphoid Malignancies Revealed by Gene Expression Profiling," *Adv. Immunol.* 87:163-208 (2005)). Thus, new therapy approaches efficient for this subtype, as well as for other subtypes, are highly desirable.

The transcription factor NF-κB controls expression of a wide range of genes involved in cell proliferation, survival, stress response, angiogenesis, and inflammation (Hacker et al., "Regulation and Function of IKK and IKK-Related Kinases," *Sci. STKE* rel3 (2006) and Hayden et al., "Shared Principles in NF-kappaB Signaling," *Cell* 132:344-362 (2008)). NF-κB activity is tightly regulated by multiple signaling pathways, and abnormal NF-κB activation has been linked to cancer development and progression (Ben-Neriah et al., "Inflammation Meets Cancer, with NF-kappaB as the Matchmaker," *Nat. Immunol.* 12:715-723 (2011); Karin, "Nuclear Factor-kappaB in Cancer Development and Progression," *Nature* 441:431-436 (2006); Karin, "NF-kappaB as a Critical Link Between Inflammation and Cancer," *Cold Spring Harb. Perspect. Biol.* 1:a000141 (2009); and Staudt, "Oncogenic Activation of NF-kappaB," *Cold Spring Harb. Perspect Biol.* 2:a000109 (2010)). Constitutive NF-κB activation has been observed in high frequency in all main DLBCL subtypes, especially in ABC DLBCLs with more than 90% of the tumors showing nuclear NF-κB, which is the hallmark of its activation (Compagno et al., "Mutations of Multiple Genes Cause Deregulation of NF-kappaB in Diffuse Large B-cell Lymphoma," *Nature* 459:717-721 (2009); Davis et al., "Chronic Active B-Cell-Receptor Signalling in Diffuse Large B-Cell Lymphoma," *Nature* 463:88-92 (2010); Honma et al., "TNFAIP3/A20 Functions as a Novel Tumor Suppressor Gene in Several Subtypes of Non-Hodgkin Lymphomas," *Blood* 114:2467-2475 (2009); Lenz et al., "Oncogenic CARD11 Mutations in Human Diffuse Large B Cell Lymphoma," *Science* 319:1676-1679 (2008); Ngo et al., "Oncogenically Active MYD88 Mutations in Human Lymphoma," *Nature* 470:115-119 (2011); and Staudt, "Oncogenic Activation of NF-kappaB," *Cold Spring Harb. Perspect Biol.* 2:a000109 (2010)). A recent genomic study revealed that more than 60% of ABC DLBCLs and about 30% of GCB DLBCLs harbor somatic mutations in multiple components of NF-κB signaling pathways, such as B-cell receptor ("BCR"), CD40, and Toll-like receptor pathways (Pasqualucci et al., "Analysis of the Coding Genome of Diffuse Large B-Cell Lymphoma," *Nat. Gen.* 43:830-837 (2011)). Importantly, it has been demonstrated that the constitutive NF-κB signaling is required for the proliferation and survival of ABC DLBCL cells lines (Davis et al., "Constitutive Nuclear Factor KappaB Activity is Required for Survival of Activated B Cell-Like Diffuse Large B Cell Lymphoma Cells," *J. Exp. Med.* 194:1861-1874 (2001); Davis et al., "Chronic Active B-Cell-Receptor Signalling in Diffuse Large B-Cell Lymphoma," *Nature* 463:88-92 (2010); Lam et al., "Small Molecule Inhibitors of Ikappab Kinase are Selectively Toxic for Subgroups of Diffuse Large B-Cell Lymphoma Defined by Gene Expression Profiling," *Clin. Cancer Res.* 11:28-40 (2005); and Ngo et al., "Oncogenically Active MYD88 Mutations in Human Lymphoma," *Nature* 470:115-119 (2011)). Collectively, these observations point to a primary role for constitutive NF-κB signaling in the pathogenesis of DLBCL. It is therefore proposed that the NF-κB signaling pathway may represent a rational therapeutic target in DLBCL (Rui et al., "Malignant Pirates of the Immune System," *Nat. Immunol.* 12:933-940 (2011) and Staudt, "Oncogenic Activation of NF-kappaB," *Cold Spring Harb. Perspect. Biol.* 2:a000109 (2010)).

Ubiquitination, the covalent attachment of ubiquitin ("Ub") molecule to target proteins, regulates diverse cellular processes. Ubiquitination proceeds through a stepwise enzymatic cascade involving three classes of enzymes: a Ub-activating enzyme ("E1"), a Ub-conjugating enzyme ("E2"), and a Ub ligase ("E3"). The E1 enzyme activates ubiquitin in an ATP-dependent manner and transfers the activated ubiquitin to an E2 enzyme through the formation of a thioester bond between the carboxy terminus of ubiquitin and the active site cysteine of the E2, generating an E2 and Ub thioester conjugate (denoted as E2~Ub). The E2 then cooperates with an E3 to attach the ubiquitin to a lysine residue of a substrate. Ubiquitin itself can serve as a substrate and the process can undergo multiple rounds, resulting in the formation of polyubiquitin chains (Pickart et al., "Ubiquitin: Structures, Functions, Mechanisms," *Biochim. Biophys. Acta.* 1695:55-72 (2004); Weissman et al., "The Predator Becomes the Prey: Regulating the Ubiquitin System by Ubiquitylation and Degradation," *Nat. Rev. Mol. Cell Biol.* 12:605-620 (2011); and Wenzel et al., "E2s: Structurally Economical and Functionally Replete," *Biochem. J.* 433:31-42 (2011)). As ubiquitin has seven lysine residues and any one of them can be conjugated to another ubiquitin, polyubiquitin chains of different linkages with distinct functional properties are formed in cells. For example, lysine 48-(K48-) linked polyubiquitin chains typically target substrates for proteasomal degradation, while K63-linked polyubiquitin chains function as scaffolds to assemble protein complexes in DNA repair and NF-κB signaling (Liu et al., "Expanding Role of Ubiquitination in NF-kappaB Signaling," *Cell Res.* 21:6-21 (2011); Panier et al., "Regulatory Ubiquitylation in Response to DNA Doublestrand Breaks," *DNA Repair* 8:436-443 (2009); Wertz et al., "Signaling to NF-kappaB: Regulation by Ubiquitination," *Cold Spring Harb. Perspect. Biol.* 2:a003350 (2010); and Ye et al., "Building Ubiquitin Chains: E2 Enzymes at Work," *Nat. Rev. Mol. Cell Biol.* 10:755-764 (2009)).

Ubc13 (also known as UBE2N) is the active subunit of an E2 enzyme that catalyzes the synthesis of K63-linked polyubiquitin chains. It functions together with one of its two cofactors, UeV1A (UBE2V) and Mms2 (UBEV2), which are E2 variants that lack the active site cysteine residues (Wenzel et al., "E2s: Structurally Economical and Functionally Replete," *Biochem. J.* 433:31-42 (2011) and Ye et al., "Building Ubiquitin Chains: E2 Enzymes at Work," *Nat. Rev. Mol. Cell Biol.* 10:755-764 (2009)). In response to the engagement of several membrane receptors, such as T-cell receptor and toll-like receptors, Ubc13-UeV1A, in conjunction with the E3 enzyme TRAF6, catalyzes the formation of K63-linked polyubiquitin chains, which interact with both TAK1 and IKK complexes and thereby bring these two kinases into proximity. Consequently, the activated TAK1 phosphorylates and activates the IKK complex, which in turn phosphorylates IκB proteins, leading to IκB protein degradation and subsequent NF-κB activation (Liu et al., "Expanding Role of Ubiquitination in NF-kappaB Signaling," *Cell Res.* 21:6-21 (2011) and Wertz et al., "Signaling to NF-kappaB: Regulation by Ubiquitination," *Cold Spring Harb. Perspect. Biol.* 2:a003350 (2010)). In complex with the Mms2 cofactor, Ubc13 promotes the K63-linked ubiquitination at sites of DNA double-strand breaks, leading to the recruitment of repair proteins to the DNA lesions (Panier et al., "Regulatory Ubiquitylation in Response to DNA Doublestrand Breaks," *DNA Repair* 8:436-443 (2009) and Ye et al., "Building Ubiquitin Chains: E2 Enzymes at Work," *Nat. Rev. Mol. Cell Biol.* 10:755-764 (2009)). In addition to participating in NF-κB activation and DNA doublestrand break repair, Ubc13 regulates other cellular processes, including nuclear localization of tumor suppressor p53 protein and MAP kinase activation (Laine et al., "Regulation of p53 Localization and Activity by Ubc13," *Mol. Cell. Biol.* 26:8901-8913 (2006); Topisirovic et al., "Control of p53 Multimerization by Ubc13 is JNK-Regulated," *Proc. Nat. Acad. Sci. U.S.A.* 106:12676-12681 (2009); and Yamamoto et al., "Key Function for the Ubc13 E2 Ubiquitin-Conjugating Enzyme in Immune Receptor Signaling," *Nat. Immunol.* 7:962-970 (2006)).

The chronic active BCR signaling, together with MYD88-mediated signaling, is largely responsible for the constitutive NF-κB activation in ABC DLBCL cells and controls the proliferation and survival of these cells. Hence, inhibition of this pathway is a target for new therapeutic strategies (Davis et al., "Chronic Active B-Cell-Receptor Signalling in Diffuse Large B-Cell Lymphoma," *Nature* 463:88-92 (2010) and Rui et al., "Malignant Pirates of the Immune System," *Nat. Immunol.* 12:933-940 (2011)). Indeed, small-molecule inhibitors of several kinases such as Syk and PKC-β, which mediate NF-κB activation in the BCR signaling pathway (Siebenlist et al., "Control of Lymphocyte Development by Nuclear Factor-kappaB," *Nat. Rev. Immunol.* 5:435-445 (2005) and Thome et al., "Antigen Receptor Signaling to NF-kappaB via CARMA1, BCL10, and MALT1," *Cold Spring Harb. Perspect. Biol.* 2:a003004 (2010)), have been tested in clinical trials with some efficacy (Dupire et al., "Targeted Treatment and New Agents in Diffuse Large B Cell Lymphoma," *Int. J. Hematol.* 92:12-24 (2010)). As both Syk and PKCβ function upstream of the CARMA1 (CARD11)-BCL10-MALT1 (CBM) complex (Siebenlist et al., "Control of Lymphocyte Development by Nuclear Factor-kappaB," *Nat. Rev. Immunol.* 5:435-445 (2005) and Thome et al., "Antigen Receptor Signaling to NF-kappaB via CARMA1, BCL10, and MALT1," *Cold Spring Harb. Perspect. Biol.* 2:a003004 (2010)), inhibition of these kinases may have limited effect on the constitutive NF-κB activation in over 10% of DLBCLs that harbor mutations in the CBM complex (Compagno et al., "Mutations of Multiple Genes Cause Deregulation of NF-kappaB in Diffuse Large B-cell Lymphoma," *Nature* 459:717-721 (2009); Lenz et al., "Oncogenic CARD11 Mutations in Human Diffuse Large B Cell Lymphoma," *Science* 319:1676-1679 (2008); and Pasqualucci et al., "Analysis of the Coding Genome of Diffuse Large B-Cell Lymphoma," *Nat. Gen.* 43:830-837 (2011)).

The present invention is directed to overcoming limitations in the art by providing new treatments for B cell malignancies.

SUMMARY OF THE INVENTION

A first aspect of the present invention relates to a method of treating B cell malignancies. This method involves administering to a subject a compound having a structure of formula (I)

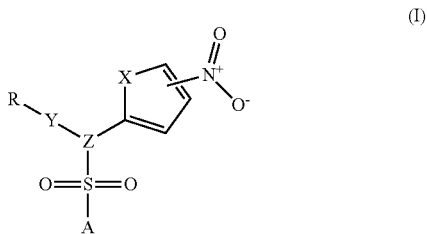

where
Z is a saturated or unsaturated hydrocarbon containing 0-5 carbon atoms;
A is an aromatic or heteroaromatic compound optionally substituted with one to five substituents selected from the group consisting of $C_1$-$C_4$ alkyl, cyano, and halo; and
X is O, S, NH, or C;
Y and R are optional;
Y, when present, is a saturated or unsaturated hydrocarbon containing 0-5 carbon atoms and is linked to any one of the carbon atoms of Z; and
R, when present, is an aromatic or heteroaromatic compound optionally substituted with one to five substituents selected from the group consisting of $C_1$-$C_4$ alkyl, cyano, and halo, to cause cell death of a B cell malignancy, thereby treating the B cell malignancy in the subject.

A second aspect of the present invention relates to a method of causing cell death of malignant B cells. This method involves introducing a compound having a structure of formula (I) as defined in the first aspect of the present invention supra, into a malignant B cell under conditions effective to cause cell death of the malignant B cell.

A third aspect of the present invention relates to a pharmaceutical composition comprising a compound having a structure of formula (I) as defined in the first aspect of the present invention supra and a drug delivery vehicle that targets lymphoma B cells for delivery of the compound.

A fourth aspect of the present invention relates to a therapeutic system comprising a compound having a structure of formula (I) as defined in the first aspect of the present invention supra and a second therapeutic agent that is useful to reduce the survival of a B cell malignancy.

A fifth aspect of the present invention relates to a compound having a structure of formula (I)

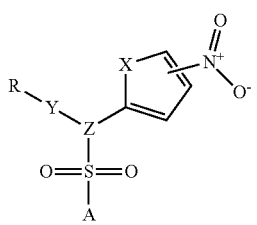

where

Z is a saturated or unsaturated hydrocarbon containing 0-5 carbon atoms;

A is an aromatic or heteroaromatic compound optionally substituted with one to five substituents selected from the group consisting of $C_1$-$C_4$ alkyl, cyano, and halo; and X is O, S, NH, or C;

Y and R are optional;

Y, when present, is a saturated or unsaturated hydrocarbon containing 0-5 carbon atoms and is linked to any one of the carbon atoms of Z; and R, when present, is an aromatic or heteroaromatic compound optionally substituted with one to five substituents selected from the group consisting of $C_1$-$C_4$ alkyl, cyano, and halo, with the proviso that (i) when Z has two carbon atoms and Y and R are not present, A is not a phenyl substituted with a single methyl group and (ii) when Z and Y each have one carbon atom, R is not a phenyl substituted with a single halogen atom.

Diffuse large B-cell lymphoma (DLBCL), the most common type of non-Hodgkin's lymphoma, remains a partially curable disease. Genetic alterations in factors that regulate NF-κB activation occur frequently in DLBCL. In fact, virtually all ABC DLBCL, which is the least curable group among the three major subtypes of this malignancy, and a substantial fraction of GCB DLBCL exhibit constitutive NF-κB pathway activity. It has been demonstrated that ABC DLBCL cells depend on such activity for proliferation and survival. Thus, inhibition of NF-κB activation in DLBCL may provide an efficient and targeted therapy. In screening for small molecule compounds that may inhibit NF-κB activation in DLBCL cells, the compound NSC697923 was identified and is shown herein to inhibit the activity of the ubiquitin-conjugating (E2) enzyme Ubc13-Uev1A. NSC697923 impedes the formation of the Ubc13 and ubiquitin thioester conjugate and the constitutive NF-κB activity in ABC DLBCL cells. More importantly, NSC697923 inhibits proliferation and survival of ABC DLBCL cells as well as GCB DLBCL cells, indicating that Ubc13-Uev1A may be crucial for DLBCL growth. Consistently, knockdown of Ubc13 expression also inhibits the survival of DLBCL cells. The results described herein indicate that the Ubc13-Uev1A E2 enzyme is a viable therapeutic target in DLBCL. In addition, compound NSC697923 may be exploited for the development of DLBCL therapeutic agents.

BRIEF DESCRIPTION OF THE DRAWINGS

FIGS. 1A-1C show that compound NSC697923 inhibits NF-κB activation induced by PMA, but not by TNFα. FIG. 1A shows the chemical structure of NSC697923. In FIG. 1B, 293T-NF-luc cells were pretreated with the indicated concentrations of NSC697923 or DMSO (final concentration 0.2%; control) for 1 hour. The cells were then stimulated with PMA (100 ng/ml) or TNFα(10 ng/ml) for 6 hours, and the green fluorescence (from GFP for normalization) and luciferase activity in the cell lysate were measured. Data were expressed as the percentage activity of the control (mean+/−standard deviation (SD); n=3). FIG. 1C shows the results of 293T-NF-Luc cells pretreated with 1 μM of NSC697923 for 1 hour before the cells were stimulated with PMA or TNFα. The cells were harvested at the indicated times after stimulation, and phosphorylation of IKK and IκBα were analyzed by western blotting. Analysis of actin was used as the loading control.

FIGS. 2A-2D show the effect of NSC697923 related compounds on NF-κB activation induced by PMA. FIG. 2A shows the structures of the NSC697923 analogs tested. In FIG. 2B, 293T-NF-luc cells were pretreated with the indicated compounds (2 μM) or DMSO (0.2%) for 1 hour. The cells were then stimulated with PMA for 20 hours or left untreated as indicated. Shown are the relative luciferase activities (mean+/−SD; n=4). The luciferase activity of the unstimulated samples was set at 1. FIG. 2C shows the structures of the Nitrofuran-containing compounds tested. In FIG. 2D, 293T-NF-luc cells were pretreated with DMSO (0.02%) or various nitrofuran-containing compounds at the indicated concentrations for 1 hour, then stimulated with PMA for 6 hours. The means of the luciferase activities relative to the DMSO pretreated (control) samples from the triplicates are shown.

FIG. 3 shows that NSC697923 inhibits NF-κB activation by multiple stimuli. SUDHL-6, RAW264.7, and MEF cells were treated with NSC697923 or DMSO (control) for 1 hour before being stimulated with the PMA (100 ng/ml), RANKL (15 ng/ml), and LPS (1.5 μg/ml) for the indicated times. The levels of IκBα phosphorylation in the indicated samples were assessed by western blotting.

FIGS. 4A-4C show that NSC697923 specifically inhibits Ubc13-mediated polyubiquitin chain synthesis in vitro. FIG. 4A shows that NSC697923 inhibits the synthesis of polyubiquitin chains catalyzed by Ubc13-Uev1A in vitro. The in vitro reaction, which contains purified E1, ubiquitin, Ubc13, and Uev1A, was carried out with or without the indicated concentrations of NSC697923. The reaction products were analyzed by a ubiquitin-specific antibody on western blots. FIG. 4B is the same as FIG. 4A, except that purified GST-TRAF6 was included as the E3 in the complete reaction as indicated. FIG. 4C shows that NSC697923 exhibits no inhibitory effect on UbcHSc-mediated polyubiquitin chain synthesis. The assay was carried out as in FIG. 4B, except that UbcHSc instead of Ubc13-Uev1A was used as the E2 in the ubiquitination reaction.

FIGS. 5A-5C show that NSC697923 inhibits formation of the Ubc13~ubiquitin thioester conjugate. FIG. 5A shows that NSC697923 has no inhibitory effect on the formation of Ubc13-Uev1A complex in vitro. Purified GST or GST-Ubc13 fusion proteins were incubated with the cell extract prepared from OCI-Ly10 cells with or without the presence of NSC697923 as indicated. The amounts of Uev1A protein associated with GST or GST-Ubc13 were analyzed by western blotting. The first lane was loaded with 8% of the input cell lysate. FIG. 5B shows that NSC697923 the formation of the Ubc13~Ub thioester conjugate. The assay was carried out as described in FIG. 4A, except that the loading buffer for SDS-PAGE gel contains no reducing agent, unless otherwise specified, and the reaction was analyzed by western blotting with a Ubc13-specific antibody. FIG. 5C shows that the formation of the UbcHSc~Ub conjugate is not inhibited by NSC697923. The assay was carried out as in FIG. 5B, except that UbcHSc, instead of Ubc13 and Uev1A, was used in the ubiquitination reaction and that a UbcHSc antibody was used for western blot analysis.

FIG. 6A shows inhibition of the Ubc13~Ub conjugate formation in DLBCL cells by NSC697923. OCI-Ly10 cells were treated with the indicated concentrations of NSC697923 for 3 hours. The levels of Ubc13~Ub conjugate were analyzed by western blotting using a Ubc13-specific antibody as described in FIG. 4B. FIG. 6B shows that NSC697923 inhibits constitutive NF-κB activation in ABC DLBCL cells. OCI-Ly10 cells were treated with DMSO (0.1%) or the indicated concentrations of NSC697923 for 3.5 hours. The levels of the indicated proteins were analyzed by western blotting with the respective antibodies.

FIG. 7A shows the effect of NSC697923 on the growth of ABC DLBCL cells. The indicated ABC DLBCL cells were seeded at $3 \times 10^5$ cells/ml in 6-well plates and cultured in the presence of DMSO (0.2%, control) or various concentrations of NSC697923 for 24 hours. The live and dead cells were counted using the trypan blue exclusion assay. Shown are the means from three separate experiments. The average number of live cells in the control was set at 100. FIG. 7B shows the results of OCI-Ly10 cells treated with the indicated concentrations of NSC697923 for 5 hours. The levels of the indicated proteins were analyzed by western blotting. For caspase 3 detection, a mixture of an antibody for the uncleaved form and an antibody specific for the cleaved form was used. In FIG. 7C, OCI-Ly10 cells were treated as in FIG. 7A. The apoptotic cells (Annexin V positive cells) were measured by flow cytometry as described in Example 1 infra. A representative result from three independent experiments is depicted. FIG. 7D shows the results of OCI-Ly10 cells treated with indicated concentrations of NSC697923 for 4.5 hours. BrdU was then added into the culture medium for 30 minutes before the cell-cycle distribution of the treated cells was analyzed as described in Example 1 infra. Shown are the averages from two independent experiments. FIG. 7E shows the results of OCI-Ly7 cells treated with indicated concentrations of NSC697923 for 4.5 hours. BrdU was then added into the culture medium for 30 minutes before the cell-cycle distribution of the treated cells was analyzed as described in Example 1 infra. Shown are the averages from two independent experiments.

In FIG. 8A, the GCB DLBCL cells were plated at the indicated cell concentrations and treated with various concentrations of NSC697923 for 24 hours. The effects of NSC697923 on the growth of these cells were analyzed as described in FIG. 7A. In FIG. 8B, the cells were plated at a concentration of $4 \times 10^5$ cells/ml and treated with NSC697923 as in FIG. 8A, and the apoptotic cells were analyzed as described in FIG. 7C.

FIG. 11A shows analysis of Ubc13 expression. OCI-Ly10 cells were infected with lentiviruses that express either shControl or shUbc13. The levels of Ubc13 protein in the infected cells were analyzed 7 days after infection by western blotting with a Ubc13-specific antibody. The amount of total protein lysates loaded on each lane is indicated. FIG. 11B shows the viability of the infected OCI-Ly10 cells measured at the indicated times after infection by trypan blue exclusion assay. FIG. 11C shows cell death of the infected OCI-Ly10 cells assessed 9 days after infection with 7AAD/Annexin V staining followed by flow cytometry analysis.

FIG. 13A shows inhibition of FK2 focus formation by NSC697923. Osteosarcoma U2OS cells were pretreated with 1 μM NSC697923 for 1 hour before γ-irradiated (10 Gy). 30 minutes after irradiation, the cells were fixed and stained with the monoclonal antibody FK2, which recognizes protein-conjugated, but not free, ubiquitin and marks the foci formed by K63-linked ubiquitinated proteins at sites of DSBs. FIG. 13B shows that NSC697923 inhibits recruitment of DNA repair proteins 53BP1 and BRCA1 to the sites of DNA double-strand breaks after ionizing radiation. U2OS cells were treated as described in FIG. 13A except that the focus formation of the indicated proteins is detected with their respective antibodies.

DETAILED DESCRIPTION OF THE INVENTION

Figure 2C:
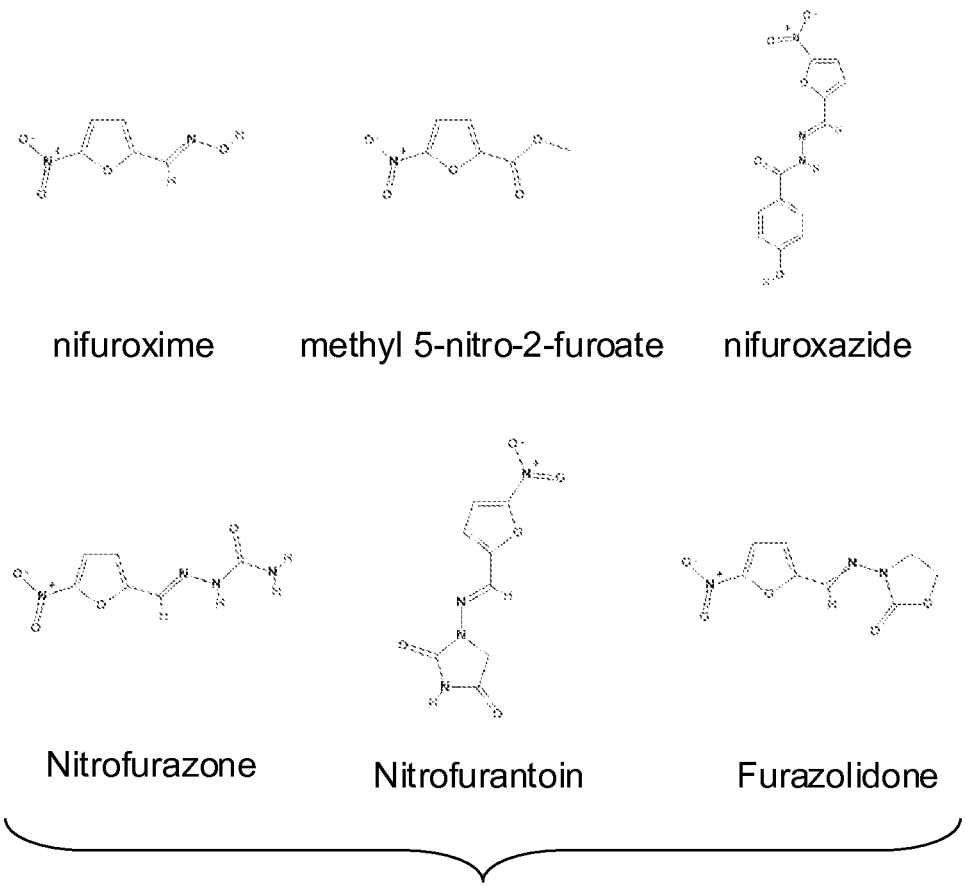

The present invention relates to methods, pharmaceutical compositions, therapeutic systems, and compounds for treating B cell malignancies. Methods, pharmaceutical compositions, therapeutic systems, and compounds of the present invention target Ubc13 in B cell malignancies. Specifically, inhibition of Ubc13 impedes NF-κB activation by multiple signaling pathways frequently mutated in B cell malignancies.

According to one aspect, the present invention is directed to a method of treating B cell malignancies. This method involves administering to a subject a compound having a structure of formula (I)

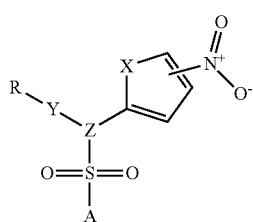

where
Z is a saturated or unsaturated hydrocarbon containing 0-5 carbon atoms;
A is an aromatic or heteroaromatic compound optionally substituted with one to five substituents selected from the group consisting of $C_1$-$C_4$ alkyl, cyano, and halo; and
X is O, S, NH, or C;
Y and R are optional;
Y, when present, is a saturated or unsaturated hydrocarbon containing 0-5 carbon atoms and is linked to any one of the carbon atoms of Z; and
R, when present, is an aromatic or heteroaromatic compound optionally substituted with one to five substituents selected from the group consisting of $C_1$-$C_4$ alkyl, cyano, and halo. Administration of an effective amount of the compound of formula (I) is sufficient to cause cell death of a B cell malignancy, thereby treating the B cell malignancy in the subject.

A related aspect of the present invention is directed to a method of causing cell death of malignant B cells. This method involves introducing a compound having a structure of formula (I), as defined supra, into a malignant B cell under conditions effective to cause cell death of the malignant B cell. The present invention may also be useful for inducing proliferation arrest.

As used herein, introducing a compound having a structure of formula (I), as defined supra, into a malignant B cell under conditions effective to cause cell death of the malignant B cell can be carried out by contacting a malignant B cell with the compound, which is then taken up by the cell (i.e., introduced) to cause cell death of the malignant B cell.

As it pertains to the compound of formula (I), aromatic or heteroaromatic groups A and R (when present) can be any single, multiple, or fused ring structures. For example, aromatic or heteroaromatic substituents include 5- or 6-membered aromatic or heteroaromatic rings containing 0-3 heteroatoms selected from O, NH, or S; a bicyclic 9- or 10-membered aromatic or heteroaromatic ring system containing 0-3 heteroatoms selected from O, NH, or S; or a tricyclic 13- or 14-membered aromatic or heteroaromatic ring system containing 0-3 heteroatoms selected from O, NH, or S. Aromatic 5- to 14-membered carbocyclic rings include, e.g., cyclopenta-1,3-diene, benzene, naphthalene, indane, tetralin, and anthracene. 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole, pyrazole, benzimidazole, pyridazine, pyrrole, imidazole, oxazole, isooxazole, indazole, isoindole, imidazole, purine, triazine, quinazoline, cinnoline, benzoxazole, acridine, benzisooxazole, and benzothiazole.

Substituted aromatic or heteroaromatic rings can include one or more substituents bonded at various positions to the one or more ring structures. Suitable substituents include $C_1$-$C_4$ alkyl, cyano, and halo. The term "halo" means halogen, including fluorine, chlorine, bromine, and iodine.

When present, Y is linked to any one of the carbon atoms of Z, e.g., via a direct carbon-carbon bond. Likewise, R, when present, is linked to any one of the carbon atoms of Y or Z (when Y is not present), e.g., via a direct carbon-carbon bond.

According to one embodiment, Z contains 0-2 carbons, A is a substituted phenyl group, X is O, and Y and R are not present. More specifically, A is substituted with a methyl group.

According to another embodiment, Z has one carbon, A is phenyl, X is O, Y has one carbon, and R is a halo-substituted phenyl. More specifically, R is substituted with a single halo group, e.g., F.

Selected compounds of formula (I) useful in the methods of the present invention include, without limitation, the compounds 2-nitro-5-tosylfuran, 2-nitro-5-(2-tosylvinyl)furan, and 2-(2-(4-fluorophenyl)-1-(phenylsulfonyl)vinyl)-5-nitrofuran, having the following structures:

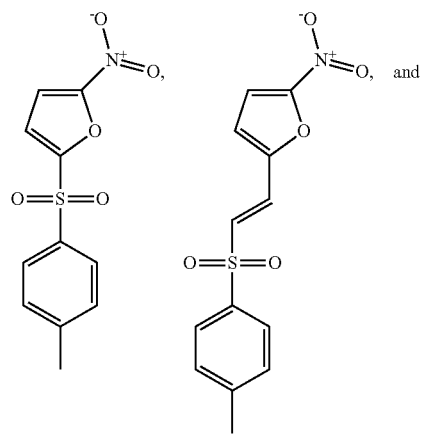

-continued

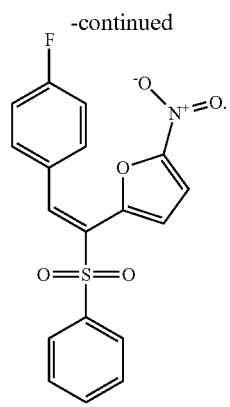

Compounds of formula (I) can be prepared by synthetic methods employed by those of ordinary skill in the art. In one embodiment, compounds of formula (I) are prepared according to methods described in, e.g., Padwa & Waterson, "A Novel Synthesis of Polysubstituted Phenols Using the SnAr Reaction of 2,5-dinitrofuran," *ARKIVOC* (iv) 29-42 (2001), which is hereby incorporated by reference in its entirety. Select compounds of formula (I) have also been described in the NCI Mechanistic Set compound library and have been prepared commercially. Alternatively, compounds of the present invention can be obtained from the National Cancer Institute Therapeutic Development Program.

In another embodiment, compounds of formula (I) are prepared according to methods described in, e.g., U.S. Pat. No. 4,243,596 to Vegh et al., which is hereby incorporated by reference in its entirety, or by analogy to methods described in Le et al., "Stereoselective One-Pot Synthesis of Vinyl Sulfones from Jethyl Phenyl Sulfone," *Synthetic Commun.* 19:2209-2212 (1989) and Nishimura et al., "Effect of Chiral Diene Ligands in Rhodium-Catalyzed Asymmetric Addition of Arylboronic Acids to α,β-Unsaturated Sulfonyl Compounds," *J. Am. Chem. Soc.* 134:9086-9089 (2012), each of which is hereby incorporated by reference in its entirety. In yet another embodiment, compounds of formula (I) can be prepared analogously to methods described in Youte et al., "Synthesis of a Thiophene Analog of Confusarine," *Lett. In Org. Chem.* 5:537-539 (2008), which is hereby incorporated by reference in its entirety.

As used herein, the treatment of a B cell malignancy is intended to encompass a reduction in the rate of proliferation of malignant B cells, compared to the absence of treatment, thereby improving quality of life and lifespan following diagnosis, as well as the complete destruction of tumor cells, which may result in remission of the B cell malignancy.

Treatment subjects can be any subject that suffers from a B cell malignancy. Preferably, the subject is a human or non-human primate, a dog, a cat, a horse, a cow, a goat, a sheep, a rabbit, or a rodent (e.g., mouse or rat).

As used herein, the term "B cell malignancy" is intended to apply to any cancerous B cell condition, such as multiple myeloma (plasma cells) or various lymphomas. Exemplary B cell lymphomas that can be treated in accordance with the present invention include, without limitation, both Hodgkin's and Non-Hodgkin's lymphomas, such as small lymphocytic lymphomas, follicular lymphomas, large cell lymphomas (e.g., diffuse large cell lymphomas (DLBCL) and diffuse mixed cell lymphomas), small non-cleaved cell lymphomas, diffuse small cell or Mantle cell lymphomas, Burkitt's lymphoma, Burkitt-like lymphoma, lymphoplasmocytic lymphoma, marginal zone lymphomas, precursor B-lymphoblastic lymphomas, etc. Various multiple myeloma types, including IgG myeloma, IgA myeloma, IgD myeloma, IgE myeloma, and light chain (κ or λ) myelomas, can be treated in accordance with the present invention. The malignant B cells to be destroyed in accordance with the present invention can be in vitro (ex vivo) or in vivo.

As used herein, and as would be understood by a person of skill in the art, the recitation of "a compound" is intended to include salts, solvates, and inclusion complexes of that compound. The term "solvate" refers to a compound of formula (I) in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: *The Science and Practice of Pharmacy* 19th Ed. (1995) volume 1, page 176-177, which is hereby incorporated by reference in its entirety. The most commonly employed inclusion complexes are those with cyclodextrins, and all cyclodextrin complexes, natural and synthetic, are specifically encompassed within the claims.

Compounds of formula (I) include "pharmaceutically acceptable salts," which means those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Compounds useful in the treatment methods of the present invention can also be present in the form of a composition that comprises a carrier, preferably a pharmaceutically acceptable carrier. Such compositions can be in solid or liquid form, such as tablets, capsules, powders, solutions, suspensions, or emulsions.

Thus, another aspect of the present invention relates to a pharmaceutical composition comprising a compound having a structure of formula (I), as described supra, and a drug delivery vehicle that targets lymphoma B cells for delivery of the compound. Such compositions and preparations should contain at least 0.1% of the compound having a structure of formula (I). The percentage of the compound having a structure of formula (I) in these compositions may, of course, be varied and may conveniently be between about 2% to about 60% of the weight of the unit. The amount of the compound having a structure of formula (I) of the present invention in such therapeutically useful compositions is such that a suitable dosage will be obtained.

The compounds of formula (I) may be orally administered, for example, with an inert diluent, or with an assimilable edible carrier, or may be enclosed in hard or soft shell capsules, or may be compressed into tablets, or may be incorporated directly with food. For oral therapeutic administration, the compounds of the present invention may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to an active ingredient, sucrose as a sweetening agent, methyl and propylparabens as preservatives, a dye, and flavoring such as cherry or orange flavor.

Administration may also be carried out parenterally. Solutions or suspensions of the compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Administration may also be carried out directly to the airways in the form of an aerosol or other inhalable formulation. For use as aerosols, the active agent in solution or suspension may be packaged in a pressurized aerosol container together with suitable propellants, for example, hydrocarbon propellants like propane, butane, or isobutane with conventional adjuvants. Active compounds also may be administered in a non-pressurized form such as in a nebulizer or atomizer. An inhalable formulation typically is in the form of an inhalable powder, which may include a pharmaceutically acceptable carrier. Suitable pharmaceutically acceptable carriers for inhalable powders may be composed of any pharmacologically inert material or combination of materials which is acceptable for inhalation. Advantageously, the carrier particles are composed of one or more crystalline sugars or one or more sugar alcohols or polyols. In one embodiment, the carrier particles are particles of dextrose or lactose. Conventional dry powder inhalers include the Rotohaler, Diskhaler, and Turbohaler. The particle size of the carrier particles may range from about 10 microns to about 1000 microns. Alternatively, the particle size of the carrier particles may range from about 20 microns to about 120 microns. In certain embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder.

Sustained release formulations include implantable devices that include a slow-dissolving polymeric matrix and one or more active compounds retained within the polymeric matrix. The matrix can be designed to deliver substantially the entire payload of the vehicle over a predetermined period of time, such as about one to two weeks up to about one to three months.

Although the formulations and compositions can also be delivered topically, it is also contemplated that the compositions can be delivered by various transdermal drug delivery systems, such as transdermal patches as known in the art.

In addition, compounds of formula (I) can be administered by using a delivery vehicle for passive or targeted delivery to particular cells. Any suitable passive or targeted delivery vehicle can be employed, including liposomes, polymeric nanoparticles, polyethylene glycol conjugates, and cell uptake peptides.

Targeting the delivery vehicle to a cell of interest is typically achieved through the use of antibodies, binding fragments thereof, or nucleic acid aptamers that are bound or suspended to the surface of the delivery vehicle. Suitable examples include, without limitation, leukemia aptamers (Shangguan et al., "Aptamers Evolved from Cultured Cancer Cells Reveal Molecular Differences of Cancer Cells in Patient Samples," *Clinical Chemistry* 53:1153-1155 (2007), which is hereby incorporated by reference in its entirety) and aptamers specific for Burkitt's lymphoma cells (Mallikaratchy et al., "Aptamer Directly Evolved from Live Cells Recognizes Membrane Bound Immunoglobin Heavy Mu Chain in Burkitt's Lymphoma Cells," *Molecular & Cellular Proteomics* 6.12:2230-2237 (2008), which is hereby incorporated by reference in its entirety). Other useful aptamers are publicly available at the Aptamer Database (Lee et al., "Aptamer Database," *Nucl. Acids Res.* 32:D95-D100 (2004), which is hereby incorporated by reference in its entirety). In addition, aptamers can be developed according to methods described to bind tumor-specific markers. Generation of aptamers specific for cancer cells has been previously described in which a modified SELEX procedure is used, with cancer cells providing one selection criteria and a substantially similar non-cancerous cell is used for negative selection (Tang et al., "Selection of Aptamers for Molecular Recognition and Characterization of Cancer Cells," *Anal. Chem.* 79(13):4900-7 (2007); Shangguan et al., "Identification of Liver Cancer-specific Aptamers Using Whole Live Cells," *Anal. Chem.* 80(3):721-8 (2008); Phillips et al., "Applications of Aptamers in Cancer Cell Biology," *Anal. Chim. Acta* 621(2):101-8 (2008), each of which is hereby incorporated by reference in its entirety).

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang et al., "pH-sensitive Immunoliposomes Mediate Target-cell-specific Delivery and Controlled Expression of a Foreign Gene in Mouse," *Proc. Natl. Acad. Sci. USA* 84:7851 (1987), which is hereby incorporated by reference in its entirety). When liposomes are endocytosed by a target cell, for example, they can be routed to acidic endosomes which will destabilize the liposome and result in drug release.

The liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety. Polymeric nanoparticles can be targeted to cell-surface markers using aptamers designed using the SELEX procedure (Farokhzad et al., "Targeted Nanoparticle-aptamer Bioconjugates for Cancer Chemotherapy In Vivo," *Proc. Natl. Acad. Sci. USA* 103(16):6315-6320 (2006), which is hereby incorporated by reference in its entirety). Nanoparticles and microparticles may comprise a concentrated core of drug that is surrounded by a polymeric shell (nanocapsules) or as a solid or a liquid dispersed throughout a polymer matrix (nanospheres). General methods of preparing nanoparticles and microparticles are described by Soppimath et al., "Biodegradable Polymeric Nanoparticles as Drug Delivery Devices," *J. Control Release* 70(1-2):1-20 (2001), which is hereby incorporated by reference in its entirety. Other polymeric delivery vehicles that may be used include block copolymer micelles that comprise a drug containing a hydrophobic core surrounded by a hydrophilic shell; they are generally utilized as carriers for hydrophobic drugs and can be prepared as found in Allen et al., "Colloids and Surfaces," *Biointerfaces* 16(1-4):3-27 (1999), which is hereby incorporated by reference in its entirety. Polymer-lipid hybrid systems consist of a polymer nanoparticle surrounded by a lipid monolayer. The polymer particle serves as a cargo space for the incorporation of hydrophobic drugs while the lipid monolayer provides a stabilizing interference between the hydrophobic core and the external aqueous environment. Polymers such as polycaprolactone and poly(D,L-lactide) may be used while the lipid monolayer is typically composed of a mixture of lipids. Suitable methods of preparation are similar to those referenced above for polymer nanoparticles. Derivatized single chain polymers are polymers adapted for covalent linkage of a biologically active agent to form a polymer-drug conjugate. Numerous polymers have been proposed for synthesis of polymer-drug conjugates including polyaminoacids, polysaccharides such as dextrin or dextran, and synthetic polymers such as N-(2-hydroxypropyl)methacrylamide (HPMA) copolymer. Suitable methods of preparation are detailed in Veronese and Morpurgo, "Bioconjugation in Pharmaceutical Chemistry," *IL Farmaco* 54(8):497-516 (1999), which is hereby incorporated by reference in its entirety.

By modifying the compounds, the compounds can be administered as a conjugate with a pharmaceutically acceptable water-soluble polymer moiety. By way of example, a polyethylene glycol conjugate is useful to increase the circulating half-life of the compound, and to reduce the immunogenicity of the molecule. Specific PEG conjugates are described in U.S. Patent Application Publ. No. 2006/0074200 to Daugs et al., which is hereby incorporated by reference in its entirety. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, Pharmaceutical Dosage Forms and Drug Delivery Systems, 5$^{th}$ Edition (Lea & Febiger 1990), Gennaro (ed.), Remington's Pharmaceutical Sciences, 19$^{th}$ Edition (Mack Publishing Company 1995), and by Ranade and Hollinger, Drug Delivery Systems (CRC Press 1996), each of which is hereby incorporated by reference in its entirety.

The compounds can be further modified to enhance cellular uptake of the compounds. For example, the compounds can be modified with a cell uptake peptide, such as HIV-1 TAT polypeptide or derivative thereof, oligoarginine polypeptide, or *Mycobacterium tuberculosis* Mce1A polypeptide (22-amino acid sequence termed Inv3), linked to the carboxy-terminal end of the peptide chain (de Coupade et al., "Novel Human-derived Cell-penetrating Peptides for Specific Subcellular Delivery of Therapeutic Biomolecules," *Biochem. J.* 390(2):407-418 (2005); U.S. Patent Application Publ. No. 2003/0032593 to Wender et al.; Wender et al., "The Design, Synthesis, and Evaluation of Molecules that Enable or Enhance Cellular Uptake: Peptoid Molecular Transporters," *Proc. Natl. Acad. Sci. U.S.A.* 97:13003-13008 (2000); Brunner et al., "Targeting DNA Mismatches with Rhodium Intercalators Functionalized with a Cell-penetrating Peptide," *Biochemistry* 45:12295-12302 (2006); Turner et al., "Synthesis, Cellular Uptake and HIV-1 Tat-dependent Trans-activation Inhibition Activity of Oligonucleotide Analogues Disulphide-conjugated to Cell-penetrating Peptides," *Nucl. Acids Res.* 33(1):27-42 (2005); Lu et al., "A Cell-penetrating Peptide Derived from Mammalian Cell Uptake Protein of *Mycobacterium tuberculosis*," *Anal. Biochem.* 353(1):7-14 (2006), each of which is hereby incorporated by reference in its entirety).

Compounds can also be administered as a conjugate with a pharmaceutically acceptable water-soluble polymer moiety. By way of example, a polyethylene glycol conjugate is useful to increase the circulating half-life of the therapeutic agent, and to reduce the immunogenicity of the molecule. Specific PEG conjugates are described in U.S. Patent Application Publ. No. 2006/0074200 to Daugs et al., which is hereby incorporated by reference in its entirety. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, PHARMACEUTICAL DOSAGE FORMS AND DRUG DELIVERY SYSTEMS, 5th Edition (Lea & Febiger 1990), Gennaro (ed.), REMINGTON'S PHARMACEUTICAL SCIENCES, 19th Edition (Mack Publishing Company 1995), and by Ranade and Hollinger, DRUG DELIVERY SYSTEMS (CRC Press 1996), each of which is hereby incorporated by reference in its entirety.

Peptide conjugates that can be used to augment cellular uptake are known in the art, and include HIV-Tat polypeptide fragments, oligoarginine, and other peptide conjugates as described in de Coupade et al., "Novel Human-derived Cell-penetrating Peptides for Specific Subcellular Delivery of Therapeutic Biomolecules," *Biochem J.* 390(Pt 2):407-418 (2005); U.S. Patent Application Publ. No. 2003/0032593 to Wender et al., each of which is hereby incorporated by reference in its entirety.

The pharmaceutical compositions of the present invention can be administered alone or in combination with other therapies, including without limitation chemotherapy agents, immunotherapy agents, radiation treatments, or combinations thereof Thus, another aspect of the present invention is directed to a therapeutic system comprising a compound having a structure of formula (I), as described supra, and a second therapeutic agent that is useful to reduce the survival of a B cell malignancy.

It is contemplated that the therapeutic agents of the present invention can be administered together with any other B cell lymphoma therapy or myeloma therapy. When two or more therapeutic agents are administered together, they can be administered simultaneously or with some delay between administration thereof (i.e., according to an optimized delivery schedule). Standard dosages of such known therapeutic agents can be administered.

Exemplary immunotherapy agents for lymphomas include rituximab (Rituxan®), Bexxar® (tositumomab with $^{131}$I) (Corixia Corp.), and Zevalin™ (ibritumomab tiuxetan with $^{111}$In or $^{90}$Y). Rituximab works by selectively depleting CD20$^+$ B cells. The therapeutic effectiveness of rituximab is described in Collins-Burow et al., "Rituximab and its Role as Maintenance Therapy in non-Hodgkin Lymphoma," *Expert Rev. Anticancer Ther.* 7(3):257-73 (2007); Marcus et al., "The Therapeutic Use of Rituximab in Non-Hodgkin's Lymphoma," *Eur. J. Haemotal. Suppl.* (67):5-14 (2007), each of which is hereby incorporated by reference in its entirety.

Other B cell lymphoma therapies include, without limitation, chemotherapies such as bleomycin (Blenoxane®), carboplatin (Paraplatin®), chlorambucil (Leukeran®), cyclophosphamide (Cytoxan®), cladribine, cytarabine (Cytosar-U®), dacarbazine (DTIC-Dome®), dexamethasone (Decadron®), doxorubicin (Adriamycin®), etoposide (Etopophos®), fludarabine (Fludara®), ifosfamide (Ifex®), methotrexate, prednisone, vincristine (Oncovin®), vinblastine, and CHOP combination therapy (described above).

Exemplary immune modulators or immunotherapy agents for myelomas include thalidomide, lenalidomide, bortezomib, and Neovastat (see Kyle and Rajkumar, "Multiple Myeloma" *Blood* 111(6):2962-2972 (2008), which is hereby incorporated by reference in its entirety).

Another aspect of the present invention relates to a compound having a structure of formula (I)

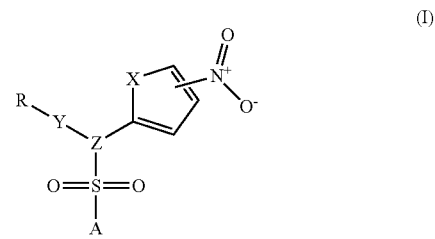

where

Z is a saturated or unsaturated hydrocarbon containing 0-5 carbon atoms;

A is an aromatic or heteroaromatic compound optionally substituted with one to five substituents selected from the group consisting of $C_1$-$C_4$ alkyl, cyano, and halo; and X is O, S, NH, or C;

Y and R are optional;

Y, when present, is a saturated or unsaturated hydrocarbon containing 0-5 carbon atoms and is linked to any one of the carbon atoms of Z; and R, when present, is an aromatic or heteroaromatic compound optionally substituted with one to five substituents selected from the group consisting of $C_1$-$C_4$ alkyl, cyano, and halo, with the proviso that (i) when Z has two carbon atoms and Y and R are not present, A is not a phenyl substituted with a single methyl group (ii) when Z and Y each have one carbon atom, R is not a phenyl substituted with a single halogen atom; and (iii) when Z, Y, and R are not present (i.e., Z has 0 carbons), A is not a phenyl substituted with a single methyl group.

According to this aspect of the present invention, compounds of formula (I) include salts, solvates, inclusion complexes, etc., as discussed supra.

EXAMPLES

The following examples are provided to illustrate embodiments of the present invention but are by no means intended to limit its scope.

Materials and Methods for Examples 1-12

Cell Culture, Chemical Compounds, and Antibodies—

HEK293T cells were grown in DMEM supplemented with 10% fetal bovine serum (FBS). Diffuse large B cell lymphoma (DLBCL) cells SUDHL-6, OCI-Ly3, OCI-Ly7, OCLLy10, and HBL-1 were cultured as previously described (Davis et al., "Constitutive Nuclear Factor KappaB Activity is Required for Survival of Activated B Cell-Like Diffuse Large B Cell Lymphoma Cells," *J. Exp. Med.* 194:1861-1874 (2001) and Kim et al., "Protein Kinase C-Associated Kinase is Required for NF-kappaB Signaling and Survival in Diffuse Large B-Cell Lymphoma Cells," *Blood* 111:1644-1653 (2008), each of which is hereby incorporated by reference in its entirety). RAW264.7 cells were cultured in α-MEM medium supplemented with 10% FBS. Mouse embryo fibroblasts ("MEFs") were prepared from day 14 embryos as previously described (Kamijo et al., "Tumor Suppression at the Mouse INK4a Locus Mediated by the Alternative Reading Frame Product p19ARF," *Cell* 91:649-659 (1997), which is hereby incorporated by reference in its entirety). MEFs with less than four passages were used for the experiments described here. Phorbol 12-myristate 13-acetate (PMA) and lipopolysaccharides (LPS) were from Sigma. TNFα and RANKL were from PeproTech, Inc. Compound NSC697923 was obtained from the NCI Developmental Therapeutic Program. Methyl 5-nitro-2-furoate, nitrofuroxazide, Nitrofurantoin, furazolidone, nitrofurazone, and nitrofuroxime were purchased from Fisher Scientific. The compounds were dissolved in DMSO, and controls in the experiments described here contain the same amounts of this solvent used for the highest tested concentrations of NSC697923. Antibodies specific for phospho-IκBα (2859), phospho-IKKα/β (2694), and cleaved caspase 3 (9661) were from Cell Signaling Technology. Antibodies specific for IκBα (sc-371), IKKα (sc-7605), Mcl-1 (sc-819), actin (sc-1616), ubiquitin (sc-8017), Uev1A (sc-47556), PARP (sc-sc-7150), and caspase 3 (sc-748) were from Santa Cruz Biotechnology. p100/p52 antibody (05-361) was from Upstate Biotechnology. Anti-Ubc13 (37-1100) and anti-UbcH5 (A-615) were from Invitrogen and Boston Biochem, respectively. Anti-GST monoclonal antibody was kindly provided by Dr. Ed Harlow (Harvard Medical School).

Generation of the NF-κB-Luciferase Reporter Cell Line—

HEK293T cells were transfected with the pNF-κB luciferase reporter construct, which contains four copies of the NF-κB binding site upstream of firefly luciferase gene (Moran et al., "Protein Kinase C-Associated Kinase can Activate NFkappaB in Both a Kinase-Dependent and a Kinase Independent Manner," *J. Biol. Chem.* 278:21526-21533 (2003), which is hereby incorporated by reference in its entirety), together with the pBabe-puro for selection. Individual clones, selected with 1.5 µg/m puromycin, were assessed for NF-κB-luciferase reporter activation by TNFα and PMA. A responsive clone was then infected with the lentivirus expressing green fluorescent protein (GFP), and the resulting 293T cells, referred to as 293T-NF-luc cells, that carry the stably integrated NF-κB-luciferase reporter and constitutively express GFP were used for compound screening.

Compound Library and High-Throughput Compound Screening—

The NCI Mechanistic Set, which includes 879 selected small-molecule compounds, was obtained from the NCI Developmental Therapeutic Program. For compound screening, 293T-NF-luc cells were seeded in 96-well plates at 30,000 cells per well in 100 µl of DMEM supplemented with 10% FBS and incubated overnight. Compounds in 100 µl of culture medium were then added into each well at a final concentration of 2 µM 1.5 hours before addition of PMA (100 ng/mL) or TNFα (10 ng/mL). Six hours after stimulation by PMA/TNFα, the cells were lysed in a solution containing 50 mM HEPES, pH 7.4, 250 mM NaCl, 1% NP40, 10% glycerol, and 1 mM DTT. After lysis, the green fluorescence of the lysates was measured using a PerkinElmer Victor2 Multilabel counter. Firefly luciferase activity of the lysates was assayed using the Promega luciferase assay reagents, as suggested by the manufacturer, and normalized to the green fluorescence readings, which were directly proportional to the cell numbers in the wells under the experimental conditions.

Preparation of GST-Ubc13 and GST-TRAF6 Proteins—

A plasmid expressing GST-Ubc13 was constructed by cloning the full-length human Ubc13 coding sequence, generated by PCR using pF1agCMV2-UbcH13 (Zou et al., "ISG15 Modification of Ubiquitin E2 Ubc13 Disrupts its Ability to Form Thioester Bond with Ubiquitin," *Biochem. Biophys. Res. Comm.* 336:61-68 (2005), which is hereby incorporated by reference in its entirety) from Addgene as the template, into a pGEX vector (Amersham). The construct was verified by DNA sequencing. The plasmid pGEX-TRAF6, which expresses GST-TRAF6 fusion protein (Lamothe et al., "Site-Specific Lys-63-Linked Tumor Necrosis Factor Receptor-Associated Factor 6 Autoubiquitination is a Critical Determinant of I kappa B Kinase Activation," *J. Biol. Chem.* 282:4102-4112 (2007), which is hereby incorporated by reference in its entirety), was kindly provided by Dr. Bryant Darnay (MD Anderson). GST-Ubc13 and GST-TRAF6 fusion proteins were expressed in *E. coli* BL21 and purified with glutathione-agarose beads (Sigma) as previously described (DeRan et al., "Transcriptional Activation of Histone Genes Requires NPAT-Dependent Recruitment of TRRAP-Tip60 Complex to Histone Promoters During the G1/S Phase Transition," *Mol. Cell Biol.* 28:435-447 (2008), which is hereby incorporated by reference in its entirety).

In Vitro Ubiquitination Assay—

The purified recombinant proteins used in the in vitro ubiquitination reactions were all purchased from Boston Biochem Inc, except GST-TRAF6, which was expressed and purified as described above. The reactions were carried out at 37° C. for 40 minutes in a buffer containing 50 mM Tris-HCl, pH 7.5, 5 mM $MgCl_2$, 200 µM ATP, 120 µM ubiquitin (U-100H), and 0.1 µM E1 (E-304). For the Ubc13-mediated ubiquitin chain synthesis, the reaction mixture includes 0.2 µM Ubc13 (E2-600) and 0.2 mM Uev1A (E2-662) with or without GST-TRAF6 as indicated. For UbcH5c-catalyzed ubiquitination, UbcH5c (E2-627), instead of Ubc13 and Uev1A, was used in the reaction. Compound NSC697923 was added into the reaction mixtures at the indicated concentrations. The reactions were terminated by the addition of an equal volume of SDSPAGE sample buffer, and the products were analyzed by western blotting with a ubiquitin specific antibody.

For detecting the E2-ubiquitin (Ubc13~Ub or UbcH5c~Ub) thioester conjugates, the reactions were carried out as described above without GST-TRAF6. The reactions were terminated with the SDS-sample buffer without a reducing agent unless specified. The products were analyzed by western blotting with an anti-Ubc13 or anti-UbcH5c antibody as indicated.

Assay for In Vitro Interaction Between Ubc13 and Uev1A—

GST-Ubc13 bound on glutathione-agarose beads was incubated with cell lysates prepared from OCI-Ly10 cells, with or without the presence of NSC697923, at 4° C. for 1 hour. The beads were washed three times with the lysis buffer (50 mM Tris-HCl (pH 8.0), 250 mM NaCl, 5 mM EDTA, 1 mM DTT, 0.2% NP-40, 5% glycerol, 0.4 mM AEBSF, 0.5 mM benzamidine-HCl, 5 µg/ml leupeptin, 5 µg/ml aprotinin, 5 µg/ml pepstatin, 10 mM NaF, 0.1 mM Na3VO4, and 50 mM β-glycerophosphate) (Zhao et al., "Expression of NPAT, a Novel Substrate of Cyclin E-CDK2, Promotes S-Phase Entry," *Genes Dev.* 12:456-461 (1998), which is hereby incorporated by reference in its entirety). The amounts of GST-Ubc13 and Uev1A proteins bound to the beads were then analyzed by western blotting.

Analyses of Cell Viability, Apoptosis, and Cell Cycle Progression—

Cell viability was measured by trypan blue exclusion assay (Invitrogen) as suggested by the manufacturer. Apoptosis was assayed using the 7AAD/annexin V apoptosis kit (BD Bioscience) as previously described (Kim et al., "Protein Kinase C-Associated Kinase is Required for NF-kappaB Signaling and Survival in Diffuse Large B-Cell Lymphoma Cells," *Blood* 111:1644-1653 (2008), which is hereby incorporated by reference in its entirety). Analysis of the cell cycle distribution of the treated cells was carried out with propidium iodide (PI) and BrdU double staining as previously described (DeRan et al., "Assessing G1-to-S-Phase Progression after Genotoxic Stress," *Methods Mol. Biol.* 782:221-230 (2011) and Su et al., "DNA Damage Induces Downregulation of Histone Gene Expression Through the G1 Checkpoint Pathway," *EMBO. J.* 23:1133-1143 (2004), each of which is hereby incorporated by reference in its entirety).

Suppression of Ubc13 Expression by RNA Interference—

The lentiviral pGIPZ constructs expressing an shRNAmir for human Ubc13 (shUbc13, RHS4430-98818339) or a non-silencing shRNAmir (shControl, RHS4346) were purchased from Open Biosystems. OCI-Ly10 cells were infected with the lentiviruses expressing shControl and shUbc13, respectively. Sixty-eight hours after transfection, the infected cells, which express GFP from the pGIPZ vector, were sorted and grown in culture medium. The expression of Ubc13 was determined by western blotting, and the cell viability at the indicated times was analyzed as described above.

Example 1

Screening for Selective Small-Molecule Compound Inhibitors of NF-κB Activation

To screen for compounds that inhibit NF-κB activation, a 293T-derived cell line that carries a stably integrated NF-κB signaling responsive luciferase reporter was established. As phorbol ester PMA, a potent PKC activator, induces NF-κB activation through a PKC-mediated pathway that relies on the CARMA1-BCL10-MALT1 complex (Baeuerle et al., "Function and Activation of NF-kappa B in the Immune System," *Annu. Rev. Immunol.* 12:141-179 (1994) and Shi et al., "Chemical Biology Strategy Reveals Pathway-Selective Inhibitor of NF-kappaB Activation Induced by Protein Kinase C," *Chem. Biol.* 5:287-299 (2010), each of which is hereby incorporated by reference in its entirety), compounds that inhibit PMA-induced NF-κB activation may impede NF-κB activation induced by chronic BCR signaling. It was then determined to identify compounds that inhibit PMA-induced NF-κB activation through compound library screening. The goal was to identify compounds with some selectivity, rather than a general inhibitor of NF-κB activation, such as an IKK inhibitor. To eliminate such compounds, a counter screening was devised in which compounds initially identified from the primary screening were tested for their effect on TNFα-induced NF-κB activation.

The NCI Mechanistic Set was screened, which contains 879 selected small molecule compounds, at a final concentration of 2 μM. In the primary screening, 109 compounds inhibited PMA-induced NF-κB activation by more than 50%. These compounds were then tested for their inhibition on NF-κB activation induced by TNFα, in parallel with their effects on PMA-induced NF-κB activation. Of these, five compounds inhibited PMA-, but not TNFα-, induced NF-κB activation in the reporter assay. One of the compounds is NSC697923, which reproducibly exhibited selective inhibitory effect on NF-κB reporter activation, as well as on endogenous NF-κB activation (FIG. 1).

Example 2

Structure-Activity Relationship Analysis

Figure 2D:
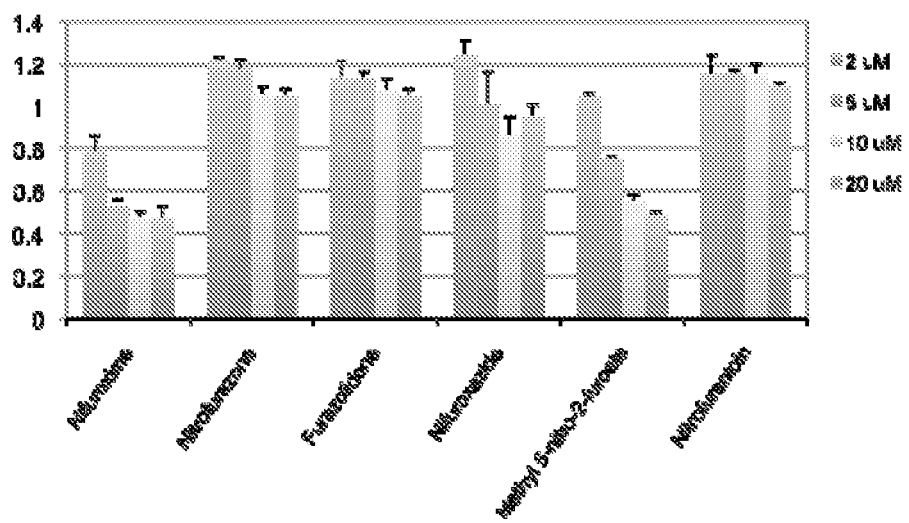

To probe the structural basis for the action of NSC697923, it was examined whether several related analogs of this compound, which are available from NCI, had a similar inhibitory activity. The compounds that contain the nitrofuran moiety inhibited PMA-induced NF-κB activation, while the compounds without this group had no such inhibitory activity (FIGS. 2A and B), indicating that the nitrofuran moiety is important for NF-κB inhibition by NSC697923. To further understand the relevance of nitrofuran group in the inhibition of NF-κB activation, a panel of commercially available nitrofuran-containing compounds was evaluated. Only some of these compounds showed an inhibitory effect on PMA-induced NF-κB activation (FIGS. 2C and 2D), indicating that an additional structure domain in NSC697923, apart from the nitrofuran moiety, is critical for its NF-κB inhibitory activity.

Example 3

Compound NSC697923 Inhibits NF-κB Activation by Multiple Stimuli

To determine the selectivity of NSC697923 further, the effect of the compound on NF-κB activation induced by other stimuli was examined. In addition to inhibiting PMA-induced NF-κB activation, NSC697923 inhibited IκBα phosphorylation by both RANKL and LPS (FIG. 3). Thus, the inhibitory activity of this compound is not limited to PMA-induced NF-κB activation. Rather, the compound inhibits NF-κB activation by multiple, albeit not all, stimuli.

Example 4

NSC697923 is an Inhibitor of the Ubiquitin Conjugating Enzyme (E2) Complex Ubc13-Uev1A Given that the ubiquitin-conjugating (E2) enzyme Ubc13-Uev1A complex is involved in NF-κB activation by multiple stimuli, including PMA, RANKL, and LPS, but not in the TNFα-induced NF-κB activation in some cells (Liu et al., "Expanding Role of Ubiquitination in NF-kappaB Signaling," *Cell Res.* 21:6-21 (2011); Wertz and Dixit, "Signaling to NF-kappaB: Regulation by Ubiquitination," *Cold Spring Harb. Perspect. Biol.* 2:a003350 (2010); Yamamoto et al., "Cutting Edge: Pivotal Function of Ubc13 in Thymocyte TCR Signaling," *Journal of Immunology* 177:7520-7524 (2006), each of which is hereby incorporated by reference in its entirety), it was reasoned that compound NSC697923 might inhibit the function of this E2 enzyme. Ubc13-Uev1A, together with a ubiquitin-activating enzyme (E1), can catalyze the synthesis of lysine 63-linked polyubiquitin chains without an E3 in vitro (Petroski et al., "Substrate Modification with Lysine 63-Linked Ubiquitin Chains Through the UBC13-UEV1A Ubiquitin-Conjugating Enzyme," *J. Biol. Chem.* 282:29936-29945 (2007) and Scheper et al., "Protein-Protein Interaction Antagonists as Novel Inhibitors of Non-Canonical Polyubiquitylation," *PLoS One* 5:e11403 (2010), each of which is hereby incorporated by reference in its entirety). It was thus tested whether NSC697923 has any effect on Ubc13-Uev1Amediated polyubiquitin chain synthesis in an in vitro assay. As shown in FIG. 4A, the compound inhibited polyubiquitin chain formation catalyzed by Ubc13-Uev1A complex in a dose-dependent manner. Although Ubc13-Uev1A can catalyze ubiquitin chain formation without an E3 enzyme, the efficiency of polyubiquitin chain synthesis is greatly enhanced in the presence of an E3, such as TRAF6 (Xia et al., "Direct Activation of Protein Kinases by Unanchored Polyubiquitin Chains," *Nature* 461:114-119 (2009), which is hereby incorporated by reference in its entirety). Therefore, the effect of NSC697923 on ubiquitin chain formation catalyzed by Ubc13-Uev1A together with TRAF6 was also examined. The ubiquitination reaction in the presence of TRAF6 is similarly inhibited by NSC697923 in a dose-dependent manner (FIG. 4B).

To investigate the specificity of NSC697923, the effect of this compound on polyubiquitin chain synthesis mediated by UbcH5c, which has high sequence homology to Ubc13 and can also catalyze the lysine 63-linked polyubiquitin chain formation in conjunction with TRAF6 (Pruneda et al., "Ubiquitin in Motion: Structural Studies of the Ubiquitin-Conjugating Enzyme Approximately Ubiquitin Conjugate," *Biochem.* 50:1624-1633 (2011), which is hereby incorporated by reference in its entirety) was examined. In contrast to the inhibition of Ubc13-Uev1A-catalyzed ubiquitination, the UbcH5c-mediated polyubiquitin chain formation was not inhibited by NSC697923 (FIG. 4C). Hence, NSC697923 is a selective inhibitor of Ubc13-Uev1A, rather than a general inhibitor of ubiquitination.

Example 5

NSC697923 Inhibits the Formation of the Ubc13-ubiquitin Thioester Conjugate

Having shown that NSC697923 is an inhibitor of the Ubc13-Uev1A E2 enzyme, the mechanism of inhibition by this compound was next explored. As both Ubc13 and UevA1 subunits are essential for the K63-linked polyubiquitin chain synthesis catalyzed by this E2 enzyme (Wenzel et al., "E2s: Structurally Economical and Functionally Replete," *Biochem. J.* 433:31-42 (2011) and Ye et al., "Building Ubiquitin Chains: E2 Enzymes at Work," *Nat. Rev. Mol. Cell Biol.* 10:755-764 (2009), each of which is hereby incorporated by reference in its entirety), NSC697923 could inhibit Ubc13-Uev1A function by blocking the dimer formation of these two subunits. To test this possibility, the effect of NSC697923 on the interaction between Ubc13 and Uev1A in a GST pull-down assay was examined. The compound showed no inhibitory effect on the complex formation between Ubc13 and Uev1A (FIG. 5A).

A critical step in ubiquitination is the formation of a thioester bond between ubiquitin (Ub) and the active site cysteine of an E2. This conjugate, referred to as E2~Ub, is the active form of an E2 enzyme and an essential intermediate for the transfer of ubiquitin to substrates (Wenzel et al., "E2s: Structurally Economical and Functionally Replete," *Biochem. J.* 433:31-42 (2011) and Ye et al., "Building Ubiquitin Chains: E2 Enzymes at Work," *Nat. Rev. Mol. Cell Biol.* 10:755-764 (2009), each of which is hereby incorporated by reference in its entirety). It was therefore investigated whether NSC697923 has any effect on Ubc13~Ub formation. While the Ubc13~Ub conjugate is readily detectable in an in vitro reaction consisting of an E1, Ubc13-Uev1A, ubiquitin, and ATP, NSC697923 inhibited formation of this thioester conjugate (FIG. 5B). Consistent with the above observation that UbcH5c-mediated ubiquitination is not blocked by NSC697923, formation of the UbcH5c~Ub conjugate is not inhibited by this compound (FIG. 5C). Thus, NSC697923 specifically inhibits the formation of Ubc13~Ub conjugate and thereby selectively impedes the Ubc13-mediated ubiquitination.

Example 6

NSC697923 Inhibits the Constitutive NF-κB Signaling in ABC DLBCL Cells

Figure 6A:
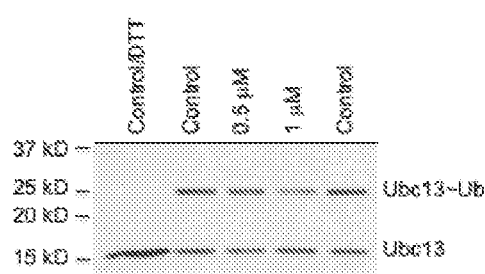
FIGS. 6A-B show that NSC697923 inhibits the constitutive NF-κB signaling in ABC-DLBCL cells.
Figure 6B:
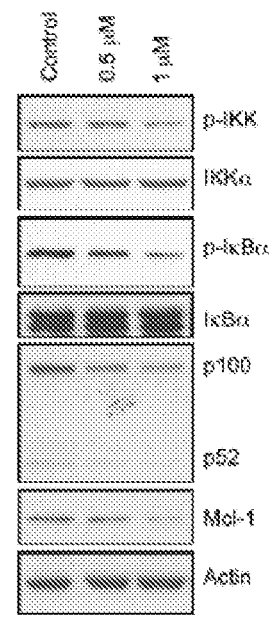

Given that Ubc13 is involved in NF-κB activation by multiple signaling pathways and that NSC697923 inhibits Ubc13 activity, it was thus investigated whether NSC697923 inhibits the constitutive NF-κB pathway activity in ABC DLBCL cells. The effect of this compound on the formation of the Ubc13~Ub conjugate in these cells was first examined. Similar to what has been observed in vitro, NSC697923 inhibited formation of the Ubc13~Ub conjugate (FIG. 6A) in OCI-Ly10 cells, an ABC DLBCL cell line, indicating that the compound also inhibits Ubc13 function in DLBCL cells. The effect of the compound on NF-κB activation was next examined NSC697923 inhibited phosphorylation of IKK and IκBα in OCI-Ly10 cells (FIG. 6B), indicating the compound induced inhibition of NF-κB activation. Consistently, expression of p100 and Mc1-1, known NF-κB targets (Lombardi et al., "Structural and Functional Characterization of the Promoter Regions of the NFKB2 Gene," *Nucleic Acids Res.* 23:2328-2336 (1995) and Shetty et al., "Transcription Factor NF-kappaB Differentially Regulates Death Receptor 5 Expression Involving Histone Deacetylase 1," *Mol. Cell. Biol.* 25:5404-5416 (2005), each of which is hereby incorporated by reference in its entirety), is inhibited in OCI-Ly10 cells treated with the compound (FIG. 6B). Thus, the results indicate that NSC697923 inhibits the constitutive NF-κB signaling in ABC DLBCL cells.

Example 7

NSC697923 Inhibits the Proliferation and Survival of ABC DLBCL Cells

Figure 7A:
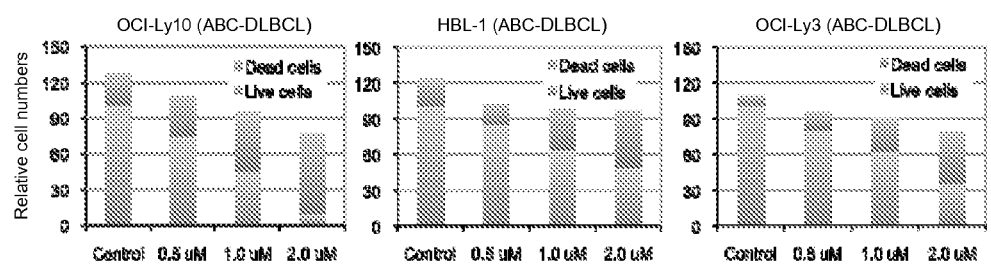
FIGS. 7A-7E show that NSC697923 inhibits the proliferation and survival of ABC DLBCL cells.
Figure 7B:
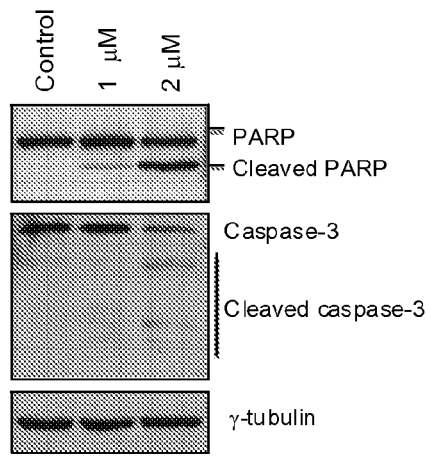
Figure 7D:
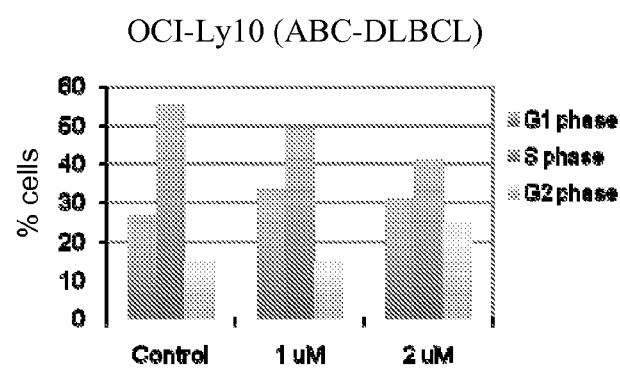
Figure 7C:
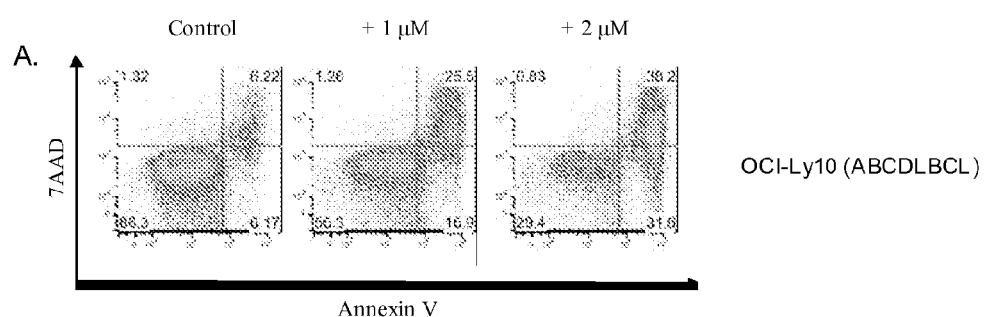

As NSC697923 inhibits NF-κB activation in ABC DLBCL cells, which depend on constitutive NF-κB activity for growth (Davis et al., "Constitutive Nuclear Factor KappaB Activity is Required for Survival of Activated B Cell-Like Diffuse Large B Cell Lymphoma Cells," *J. Exp. Med.* 194:1861-1874 (2001); Lam et al., "Small Molecule Inhibitors of Ikappab Kinase are Selectively Toxic for Subgroups of Diffuse Large B-Cell Lymphoma Defined by Gene Expression Profiling," *Clin. Cancer Res.* 11:28-40 (2005); and Staudt, "Oncogenic Activation of NF-kappaB," *Cold Spring Harb. Perspect Biol.* 2:a000109 (2010), each of which is hereby incorporated by reference in its entirety), the effect of this compound on the proliferation and survival of these cells was investigated. In line with the observation that ABC DLBCL cells rely on constitutive NF-κB activity for survival, NSC697923 induced proliferation arrest and cell death of ABC DLBCL cells, including OCI-Ly3 cells which carry a mutated CARMA1 (CARD11) (Lenz et al., "Oncogenic CARD11 Mutations in Human Diffuse Large B Cell Lymphoma," *Science* 319:1676-1679 (2008), which is hereby incorporated by reference in its entirety) (FIG. 7A). Treatment of OCI-Ly10 cells with the compound resulted in activation of caspase 3, cleavage of PARP, and the increase in annexin V-positive cells (FIGS. 7B and 7C), hallmarks of apoptosis (Kim et al., "Protein Kinase C-Associated Kinase is Required for NF-kappaB Signaling and Survival in Diffuse Large B-Cell Lymphoma Cells," *Blood* 111:1644-1653 (2008), which is hereby incorporated by reference in its entirety). Thus, NSC697923 induces apoptosis in ABC DLBCL cells.

Figure 7E:
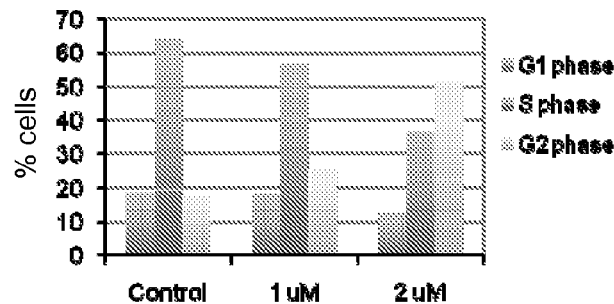

To confirm that NSC697923 indeed inhibits proliferation, the effect of NSC697923 on cell cycle progression of OCI-Ly10 cells was examined. As long treatment of ABC DLBCL cells with NSC697923 leads to massive cell death (FIGS. 7A-7C) and may thus interfere with cell cycle analysis, cell cycle progression analysis was carried out with a short time (5 hour) treatment. Treatment of OCI-Ly10 cells and OCI-Ly7 cells with the compound resulted in a marked decrease of cells in S phase (FIGS. 7D and 7E), indicating that NSC697923 inhibits cell cycle progression in both ABC DLBCL cells and GCB DLBCL cells.

Example 8

NSC697923 Also Inhibits Proliferation and Survival of GCB DLBCL Cells

Figure 8A:
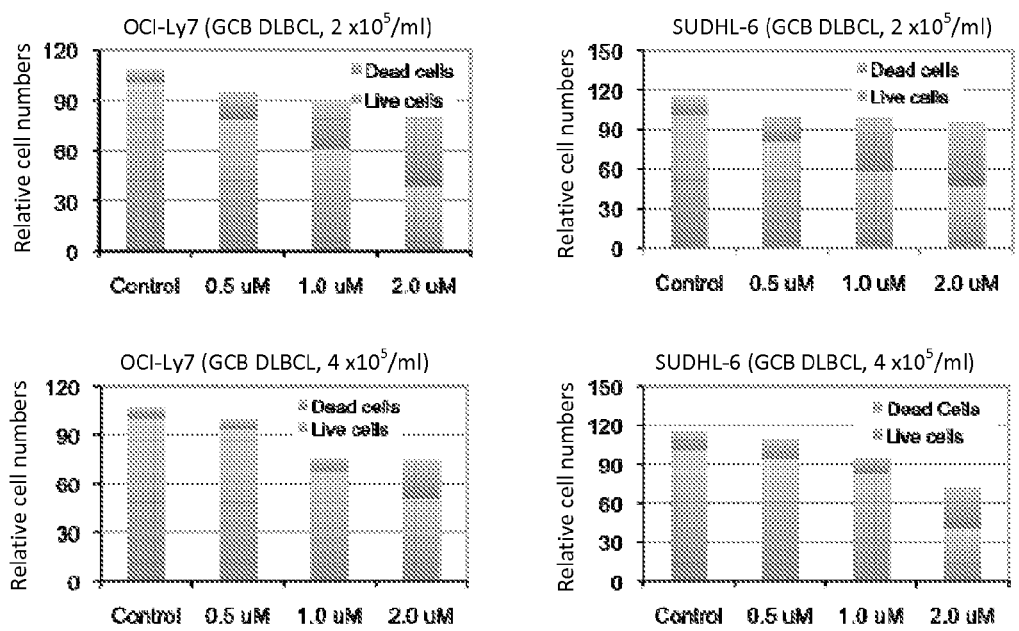
FIGS. 8A-B show that NSC697923 inhibits the proliferation and survival of GCB DLBCL cells.
Figure 8B:
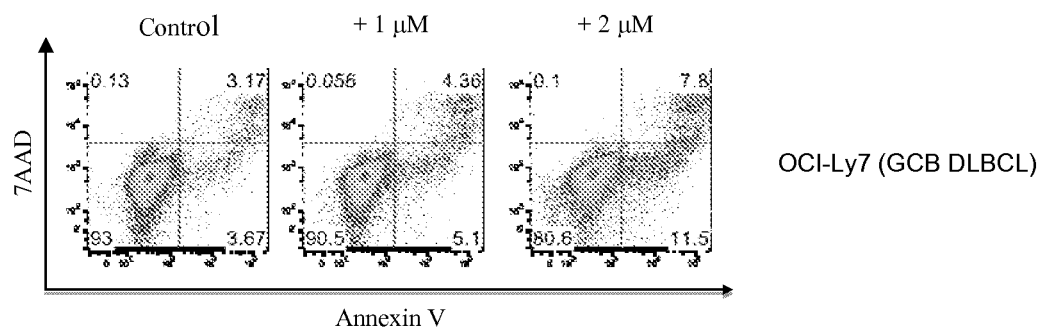

The observation that NSC697923 inhibited the proliferation and survival of ABC DLBCL cells prompted the investigation of whether this compound has similar inhibitory effects on GCB DLBCL cells, which are independent of NF-κB activity (Davis et al., "Constitutive Nuclear Factor KappaB Activity is Required for Survival of Activated B Cell-Like Diffuse Large B Cell Lymphoma Cells," *J. Exp. Med.* 194:1861-1874 (2001) and Lam et al., "Small Molecule Inhibitors of Ikappab Kinase are Selectively Toxic for Subgroups of Diffuse Large B-Cell Lymphoma Defined by Gene Expression Profiling," *Clin. Cancer Res.* 11:28-40 (2005), each of which is hereby incorporated by reference in its entirety). As shown in FIG. 8, NSC697923 also inhibited proliferation and survival of OCI-Ly7 and SUDHL-6, two GCB DLBCL cell lines. Thus, NSC697923 apparently blocks an essential pathway, other than NF-κB signaling, in GCB DLBCL cells.

Example 9

NSC697923 Reduces the Viability of Primary DLBCL Cells

Figure 9:
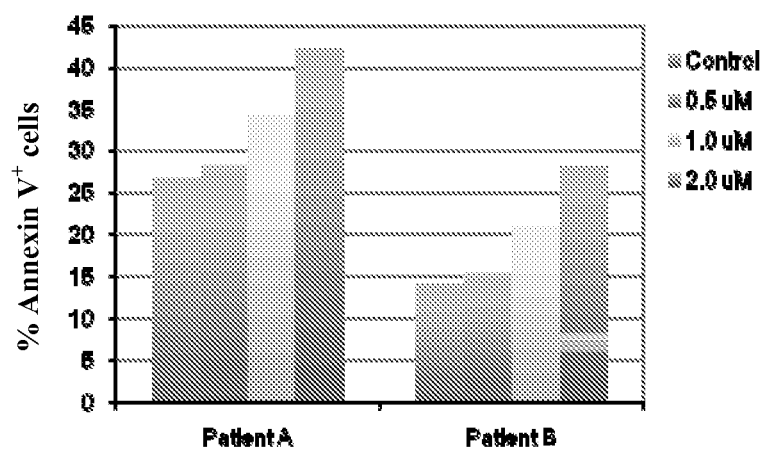
FIG. 9 shows that NSC697923 induces cell death of primary DLBCL cells. The primary cancer cells, prepared from two DLBCL patients and grown in culture medium for seven days, were seeded at $4.5 \times 10^5$ cells/mL and treated with the indicated concentrations of NSC697923 for 24 hours. The apoptotic cells were analyzed as described in FIG. 7C. Shown are the averages from two independent experiments.

In addition to the DLBCL cell lines, the effect of NSC697923 on the survival of primary DLBCL cells was tested. Primary DLBCL cells were obtained from two of the tested DLBCL patient samples that were able to grow for more than seven days in an in vitro culture condition. Treatment of these primary DLBCL cells with the compound resulted in an increase in Annexinpositive (apoptotic) cells (FIG. 9), indicating that NSC697923 also induces apoptosis of primary DLBCL cells.

Example 10

Figure 10:
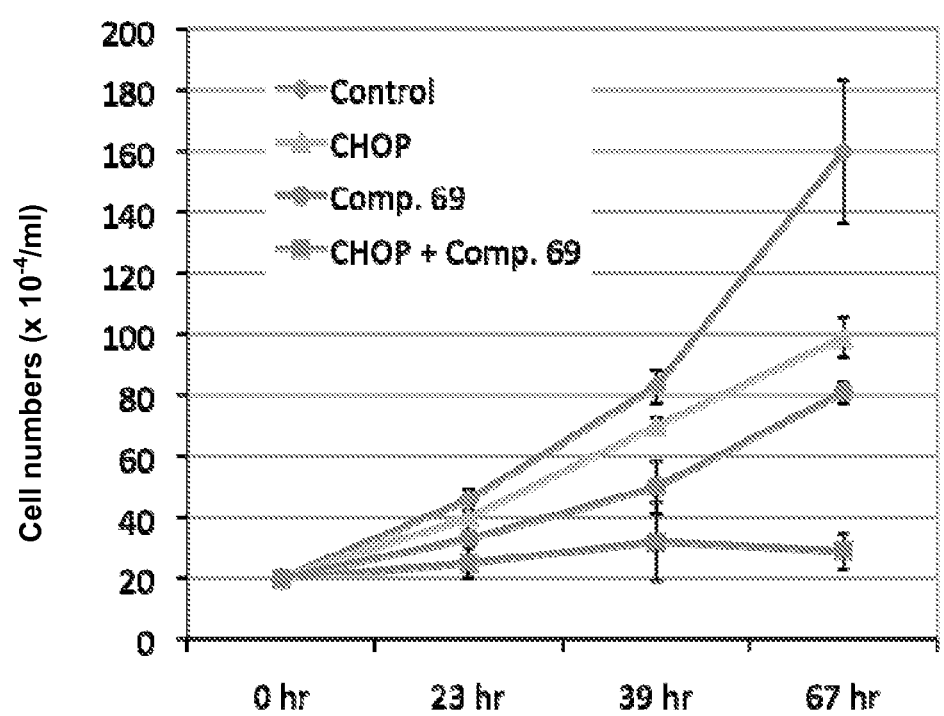
FIG. 10 shows the effect of the combination of NSC697923 and CHOP agents on the growth of DLBCL cells. OCI-Ly10 cells seeded at $3 \times 10^5$ cells/ml were treated with NSC697923 (1 μM) alone, CHOP agents, or a combination of NSC697923 and CHOP agents (the CHOP agents used here include cyclophosphamide monophosphate, doxorubicin, vincristine, and prednisone at concentrations of 5.84 pM, 1.5 pM, 260 pM, and 1.0 μM, respectively (Kim et al., "Protein Kinase C-Associated Kinase is Required for NF-kappaB Signaling and Survival in Diffuse Large B-Cell Lymphoma Cells," *Blood* 111:1644-1653 (2008) and Mohammad, et al., "Genistein Sensitizes Diffuse Large Cell Lymphoma to CHOP (Cyclophosphamide, Doxorubicin, Vincristine, Prednisone) Chemotherapy," *Mol. Cancer Ther.* 2:1361-1368 (2003), each of which is hereby incorporated by reference in its entirety). Shown are the live cells (mean+/−SD; n=3) measured with the trypan blue exclusion assay.

The Combination of NSC697923 and Chemotherapeutic Agents CHOP Leads to Increased Toxicity to DLBCL Cells As NSC697923 acts apparently through mechanisms different than that of CHOP, a combination of four agents: cyclophosphamide, doxorubicin, vincristine, and prednisone, which is commonly used for treatment of DLBCL (Friedberg and Fisher, "Diffuse Large B-cell Lymphoma," *Hematol. Oncol. Clin. North Am.* 22:941-952 (2008), which is hereby incorporated by reference in its entirety), it is possible that the combination of NSC697923 and CHOP agents may lead to enhanced toxicity to DLBCL cells. To test this possibility, OCI-Ly10 cells were treated with a combination of NSC697923 and the CHOP agents and the effect of the CHOP agents on cell viability was compared with that of NSC697923 or CHOP treatment alone. The combination of NSC697923 and the CHOP agents had additive toxicity to OCI-Ly10 cells (FIG. 10), indicating that incorporation of a Ubc13 inhibitor into the CHOP regimen may increase efficacy of DLBCL treatment.

Example 11

Knockdown of Ubc13 Induces Cell Death of DLBCL Cells

Figure 11A:
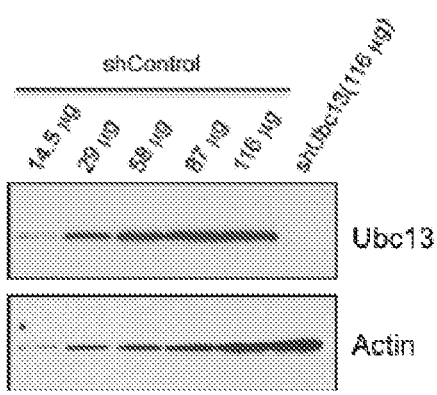
FIGS. 11A-11C show that suppression of Ubc13 expression induces cell death of DLBCL cells.
Figure 11C:
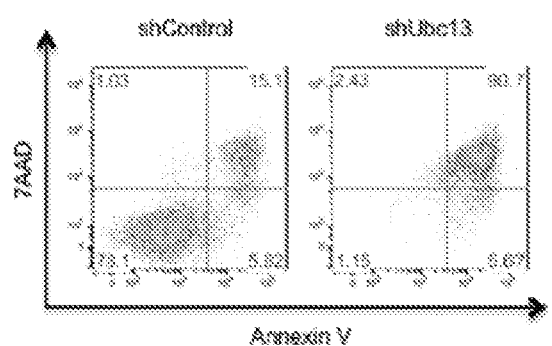
Figure 11B:
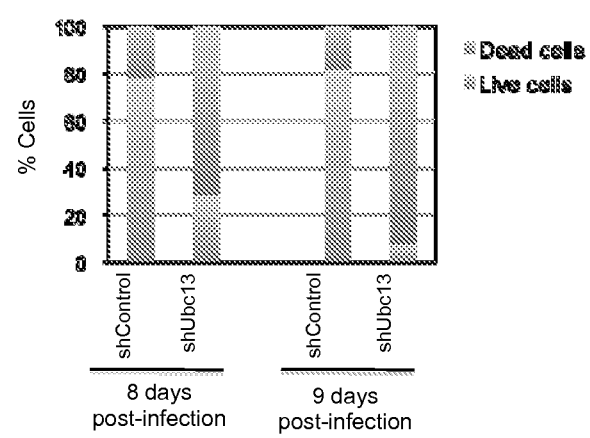

The above studies on NSC697923 indicate that Ubc13 plays a crucial role in the proliferation and survival of DLBCL cells. To test this possibility further, it was examined whether Ubc13 expression is required for the survival of DLBCL cells. The microRNA-derived shRNAs from a lentiviral vector were employed to knockdown the expression of Ubc13 (FIG. 11A). Suppression of Ubc13 expression leads to a dramatic increase in the cell death of DLBCL cells (FIGS. 11B and 11C), supporting the idea that Ubc13 is essential for survival of DLBCL cells.

Discussion of Examples 1-11

Despite recent advances in treatment, a significant proportion of DLBCL patients, especially ABC DLBCL patients, still die of this malignancy (Mahadevan et al., "Novel Therapeutics for Aggressive Non-Hodgkin's Lymphoma," *J. Clin. Oncol.* 29:1876-1884 (2011) and Staudt et al., "The Biology of Human Lymphoid Malignancies Revealed by Gene Expression Profiling," *Adv. Immunol.* 87:163-208 (2005), each of which is hereby incorporated by reference in its entirety). Development of new therapies targeting pathways essential for the proliferation and survival of the ABC subgroup, as well as the GCB subtype, may improve the clinical outcomes. Here the identification of a small-molecule compound inhibitor of the ubiquitin-conjugating (E2) enzyme Ubc13-Uev1A is reported, and this compound, NSC697923, is shown to induce proliferation arrest and apoptosis in both ABC and GCB DLBCL cell lines, as well as apoptosis in primary DLBCL cells. These results, together with the observation that Ubc13 knockdown inhibits the survival of DLBCL cells, indicate that Ubc13 is crucial for the proliferation and survival of DLBCL cells. Thus, Ubc13/Uev1A may represent a potential therapeutic target for DLBCL.

Figure 12:
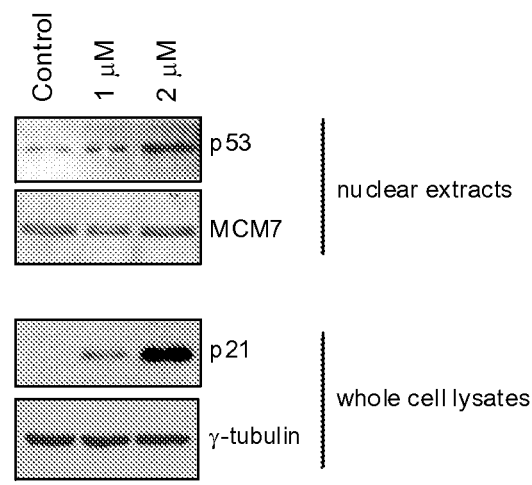
FIG. 12 shows that NSC697923 increases nuclear accumulation of p53 and p21 expression. OCI-Ly10 cells were treated with indicated concentrations of NSC697923 for 3.5 hours. The level of p53 in the nuclear extract and the level of p21 in the whole cell lysates were analyzed by western blotting.

The cytotoxic effect of NSC697923 on ABC DLBCL cells likely results, at least in part, from the inhibition of NF-κB signaling, known to be essential for the proliferation and survival of these cells (Davis et al., "Constitutive Nuclear Factor KappaB Activity is Required for Survival of Activated B Cell-Like Diffuse Large B Cell Lymphoma Cells," *J. Exp. Med.* 194:1861-1874 (2001); Davis et al., "Chronic Active B-Cell-Receptor Signalling in Diffuse Large B-Cell Lymphoma," *Nature* 463:88-92 (2010); Lam et al., "Small Molecule Inhibitors of Ikappab Kinase are Selectively Toxic for Subgroups of Diffuse Large B-Cell Lymphoma Defined by Gene Expression Profiling," *Clin. Cancer Res.* 11:28-40 (2005); and Ngo et al., "Oncogenically Active MYD88 Mutations in Human Lymphoma," *Nature* 470:115-119 (2011), each of which is hereby incorporated by reference in its entirety). As Ubc13 negatively regulates nuclear localization of p53 (Laine et al., "Regulation of p53 Localization and Activity by Ubc13," *Mol. Cell. Biol.* 26:8901-8913 (2006), which is hereby incorporated by reference in its entirety), which can inhibit both cell proliferation and survival (Lane et al., "p53 Research: The Past Thirty Years and the Next Thirty Years," *Cold Spring Harb. Perspect. Biol.* 2:a000893 (2010); Vousden et al., "Blinded by the Light: The Growing Complexity of p53," *Cell* 137:413-431 (2009), each of which is hereby incorporated by reference in its entirety), NSC697923 may also exert its effect through p53 activation. Indeed, it was found that NSC697923 treatment increased the nuclear level of p53 protein and p21 expression in OCI-Ly10 cells (FIG. 12). Notably, NSC697923 is also toxic to GCB DLBCL cells, such as OCI-Ly7 cells, which are independent of NF-κB activity for proliferation and survival (Davis et al., "Constitutive Nuclear Factor KappaB Activity is Required for Survival of Activated B Cell-Like Diffuse Large B Cell Lymphoma Cells," *J. Exp. Med.* 194:1861-1874 (2001) and Lam et al., "Small Molecule Inhibitors of Ikappab Kinase are Selectively Toxic for Subgroups of Diffuse Large B-Cell Lymphoma Defined by Gene Expression Profiling," *Clin. Cancer Res.* 11:28-40 (2005), each of which is hereby incorporated by reference in its entirety) and lack functional p53 (Chang et al., "Constitutive Production of the Interleukins IL-5 and IL-6 by the Lymphoma Cell Line OCI-Ly 17 Derived from a Patient with Malignant Lymphoma and Hypereosinophilia," *Leukemia & Lymphoma* 8:97-107 (1992) and Farrugia et al., "Alterations of the p53 Tumor Suppressor Gene in Diffuse Large Cell Lymphomas with Translocations of the c-MYC and BCL-2 proto-oncogenes," *Blood* 83:191-198 (1994), each of which is hereby incorporated by reference in its entirety). This observation suggests that NSC697923 targets a cellular process, other than NF-κB and p53 signaling, which is crucial for GCB DLBCL cell growth. One potential target of NSC697923 in these cells may be the MAP kinase pathway(s), which depend on Ubc13 for activation in mouse B cells (Yamamoto et al., "Key Function for the Ubc13 E2 Ubiquitin-Conjugating Enzyme in Immune Receptor Signaling," *Nat. Immunol.* 7:962-970 (2006), which is hereby incorporated by reference in its entirety). Therefore, NSC697923 may inhibit cell proliferation and survival through several different mechanisms.

A previous study reported that the natural compound leucettamol A and one of its derivatives inhibited the complex formation between Ubc13 and Uev1A in vitro (Tsukamoto et al., "Leucettamol A: A New Inhibitor of Ubc13-Uev1A Interaction Isolated from a Marine Sponge, *Leucetta aff. microrhaphis,*" *Bioorg. Med. Chem. Lett.* 18:6319-6320 (2008), which is hereby incorporated by reference in its entirety). The biological effects of these compounds, however, were not described. Another study showed that a peptidometic molecule developed through combinatorial peptoid library screening disrupted the interaction between Ubc13 and Uev1A in vitro and inhibited the invasiveness and tumor growth of a prostate cancer cell line (Scheper et al., "Protein-Protein Interaction Antagonists as Novel Inhibitors of Non-Canonical Polyubiquitylation," *PLoS One* 5:e11403 (2010), which is hereby incorporated by reference in its entirety). It has been suggested that these three compounds are not suitable lead compounds for the development of therapeutics because they do not possess drug-like properties (Madiraju et al., "TR-FRET-Based High-Throughput Screening Assay for Identification of UBC13 Inhibitors," *J. Biomol. Screen.* 17(2):163-176 (2012), which is hereby incorporated by reference in its entirety). A recent study described a TR-FRET-based high-throughput assay for identification of Ubc13 inhibitors. The authors reported that screening a NIH library of approximately 330,000 compounds at 20 μM has yielded large numbers of hits, with a positive rate of 0.089% after verification and counter-screening (Madiraju et al., "TR-FRET-Based High-Throughput Screening Assay for Identification of UBC13 Inhibitors," *J. Biomol. Screen.* 17(2):163-176 (2012), which is hereby incorporated by reference in its entirety), although they did not report the identities of these hits. As the assay relied on ubiquitin chain synthesis, compounds such as inhibitors of the E1 enzyme, would also be scored as positives in the screening. It thus remains to be sorted out which hits are truly inhibitors of Ubc13.

In these examples it is shown that NSC697923 is a specific inhibitor of Ubc13, which acts through inhibiting the formation of the Ubc13~Ub conjugate. The structure-activity relationship studies described herein suggest that the nitrofuran group is important, but not sufficient, for the inhibition of Ubc13 activity. Several nitrofuran-containing pyrazolidine compounds were shown to inhibit the activity of the ubiquitin-activating enzyme (E1), but not E2, by blocking the formation of the E1~ubiquitin conjugate (Xu et al., "The Ubiquitin-Activating Enzyme E1 as a Therapeutic Target for the Treatment of Leukemia and Multiple Myeloma," *Blood* 115:2251-2259 (2010) and Yang et al, "Inhibitors of Ubiquitin-Activating Enzyme (E1), a New Class of Potential Cancer Therapeutics," *Cancer Res.* 67:9472-9481 (2007), each of which is hereby incorporated by reference in its entirety). Thus, it may be possible that the nitrofuran moiety of these pyrazolidine compounds and NSC697923 interfere with the thioester bound formation between the ubiquitin molecule and the active site cysteine residue of an E1 or E2 enzyme, while the remaining structures of these compounds direct them to a specific ubiquitination enzyme.

The observation that NSC697923 inhibits the constitutive NF-κB signaling in ABC DLBCL cells (FIG. 6) suggests that Ubc13-Uev1A is a crucial regulator of the NF-κB activity in these cells. Given that the constitutive NF-κB activation in these cell are controlled by chronic BCR signaling and oncogenic MYD88 signaling (Davis et al., "Chronic Active B-Cell-Receptor Signalling in Diffuse Large B-Cell Lymphoma," *Nature* 463:88-92 (2010); Ngo et al., "Oncogenically Active MYD88 Mutations in Human Lymphoma," *Nature* 470:115-119 (2011); and Rui et al., "Malignant Pirates of the Immune System," *Nat. Immunol.* 12:933-940 (2011), each of which is hereby incorporated by reference in its entirety), the results suggest that Ubc13-Uev1A may play a role in these signaling pathways. Consistent with this idea, it was previously shown that Ubc13 functions in NF-κB activation downstream of MYD88 in IL-1R and TLR signaling pathways (Liu et al., "Expanding Role of Ubiquitination in NF-kappaB Signaling," *Cell Res.* 21:6-21 (2011) and Yamazaki et al., "Two Mechanistically and Temporally Distinct NFkappaB Activation Pathways in IL-1 Signaling," *Sci. Signal* 2:ra66 (2009), each of which is hereby incorporated by reference in its entirety). It is shown here that NSC697923 inhibits NF-κB activation induced by PMA (FIGS. 1 and 3), an activator of PKCβ, which is essential for BCR-induced NF-κB activation (Leitges et al, "Immunodeficiency in Protein Kinase cbeta-Deficient Mice," *Science* 273:788-791 (1996) and Su et al., "PKC-beta Controls I kappa B Kinase Lipid Raft Recruitment and Activation in Response to BCR Signaling," *Nat. Immunol.* 3:780-786 (2002), each of which is hereby incorporated by reference in its entirety). This result, together with a previous report that Ubc13 deficiency impairs PMA-induced NF-κB activation (Yamamoto et al., "Cutting Edge: Pivotal Function of Ubc13 in Thymocyte TCR Signaling," *J. Immunol.* 177:7520-7524 (2006), which is hereby incorporated by reference in its entirety), lends support for a role of Ubc13-Uev1A in BCR-induced NF-κB activation. It is worth noting that the conditional deletion of Ubc13 in mouse B cells apparently had little effect on BCR-induced NF-κB activation (Yamamoto et al., "Key Function for the Ubc13 E2 Ubiquitin-Conjugating Enzyme in Immune Receptor Signaling," *Nat. Immunol.* 7:962-970 (2006), which is hereby incorporated by reference in its entirety). Thus, Ubc13 may have acquired a lymphoma-specific function. Alternatively, the reported lack of effect of Ubc13-deficiency on NF-κB activation in mouse B cells may result from the incomplete deletion of Ubc13 in these cells (Yamamoto et al., "Cutting Edge: Pivotal Function of Ubc13 in Thymocyte TCR Signaling," *J. Immunol.* 177:7520-7524 (2006), which is hereby incorporated by reference in its entirety).

Figure 13A:
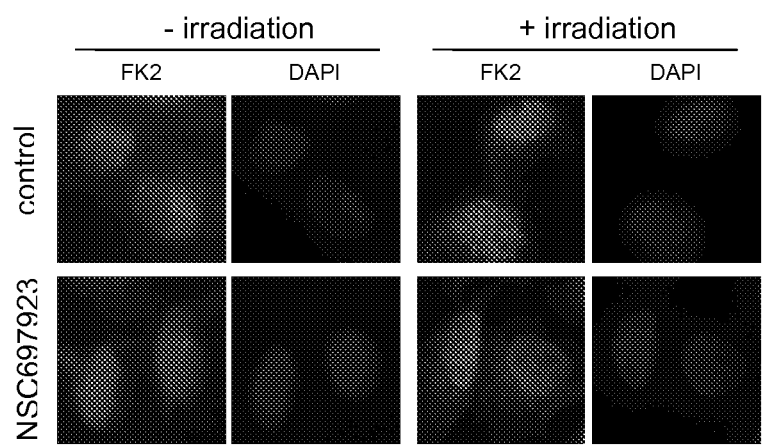
FIGS. 13A-13B show that NSC697923 inhibits DNA double-strand break (DSB) induced K63-linked ubiquitination and the recruitment of essential repair proteins to the sites of DNA doublestrand breaks.
Figure 13B:
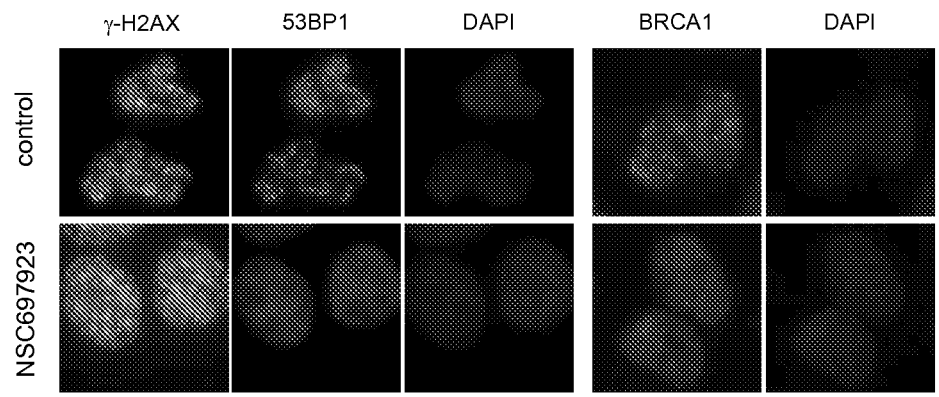
Figure 14:
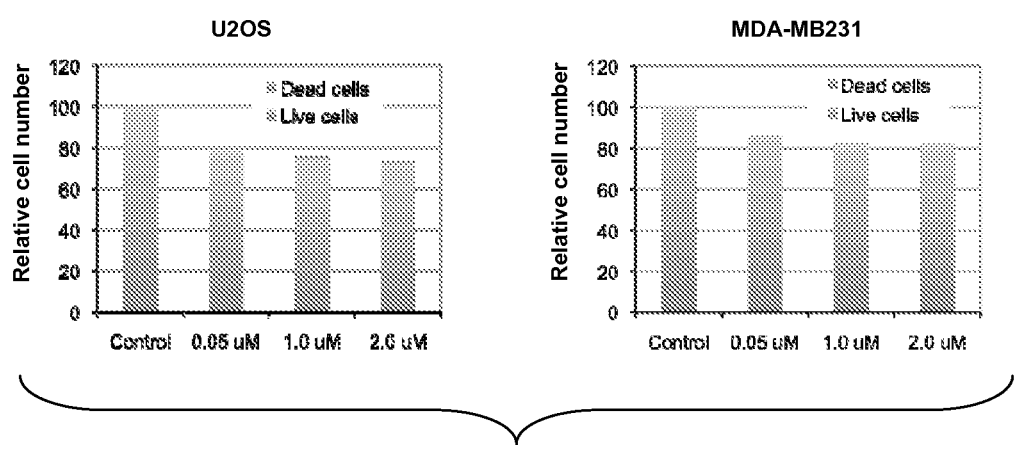
FIG. 14 shows the effect of NSC697923 on osteosarcoma U2OS and breast cancer MDA-MB231 cells. $1 \times 10^6$ cells were plated in 10 cm plates and cultured overnight. The indicated concentrations of NSC697923 were then added into culture medium for 24 hours before the cell viability was analyzed by trypan blue exclusion assay. Shown are the averages from three independent experiments.

The results described herein indicate that both the ABC and GCB subtypes of DLBCL cells depend on Ubc13 for proliferation and survival, raising the possibility that inhibition of Ubc13 function therapeutically may provide an effective treatment for DLBCL. Targeting Ubc13 in DLBCL may offer a number of advantages. As Ubc13 likely functions downstream of BCR and MYD88 signaling pathways in DLBCL cells, inhibition of Ubc13 may block DLBCL proliferation and survival promoted by the oncogenic mutations of MYD88 and the components of chronic BCR signaling, which are among the most frequently observed mutations in DLBCL (Compagno et al., "Mutations of Multiple Genes Cause Deregulation of NF-kappaB in Diffuse Large B-cell Lymphoma," *Nature* 459:717-721 (2009); Davis et al., "Chronic Active B-Cell-Receptor Signalling in Diffuse Large B-Cell Lymphoma," *Nature* 463:88-92 (2010); Lenz et al., "Oncogenic CARD11 Mutations in Human Diffuse Large B Cell Lymphoma," *Science* 319: 1676-1679 (2008); Ngo et al., "Oncogenically Active MYD88 Mutations in Human Lymphoma," *Nature* 470:115-119 (2011); and Pasqualucci et al., "Analysis of the Coding Genome of Diffuse Large B-Cell Lymphoma," *Nat. Gen.* 43:830-837 (2011), each of which is hereby incorporated by reference in its entirety). Also, inhibition of Ubc13 can potentially increase tumor suppressor p53 activity in DLBCL cells that harbor wildtype p53 protein. In addition, as Ubc13 plays a critical role in DNA double-strand break repair, inhibition of Ubc13 may sensitize radiation therapy or chemotherapy. Indeed, it was found that NSC697923 inhibits recruitment of DNA repair proteins to the sites of DNA double-streaks in mammalian cells (FIGS. 13A-13B) and exhibits an additive effect with CHOP agents (FIG. 11). Thus, development of therapeutic agents targeting Ubc13 may provide promising novel treatment for DLBCL. The studies described herein on NSC697923 may be explored for this purpose. One concern for targeting Ubc13 would be the potential side effects it may generate, as Ubc13 is involved in multiple signaling pathways. Interestingly, NSC697923, as well as knockdown of Ubc13, has much less toxic effects on the proliferation and survival of a number of other cells, such as breast cancer and osteosarcoma cells, as compared to its effect on DLBCL cells (FIG. 14). It thus appears that not all cells require Ubc13 for survival, thereby providing an opportunity to target this E2 enzyme in DLBCL with tolerable side effects.

Example 12

Effect of NSC697923 on Multiple Myeloma Cell Proliferation and Survival

Figure 15:
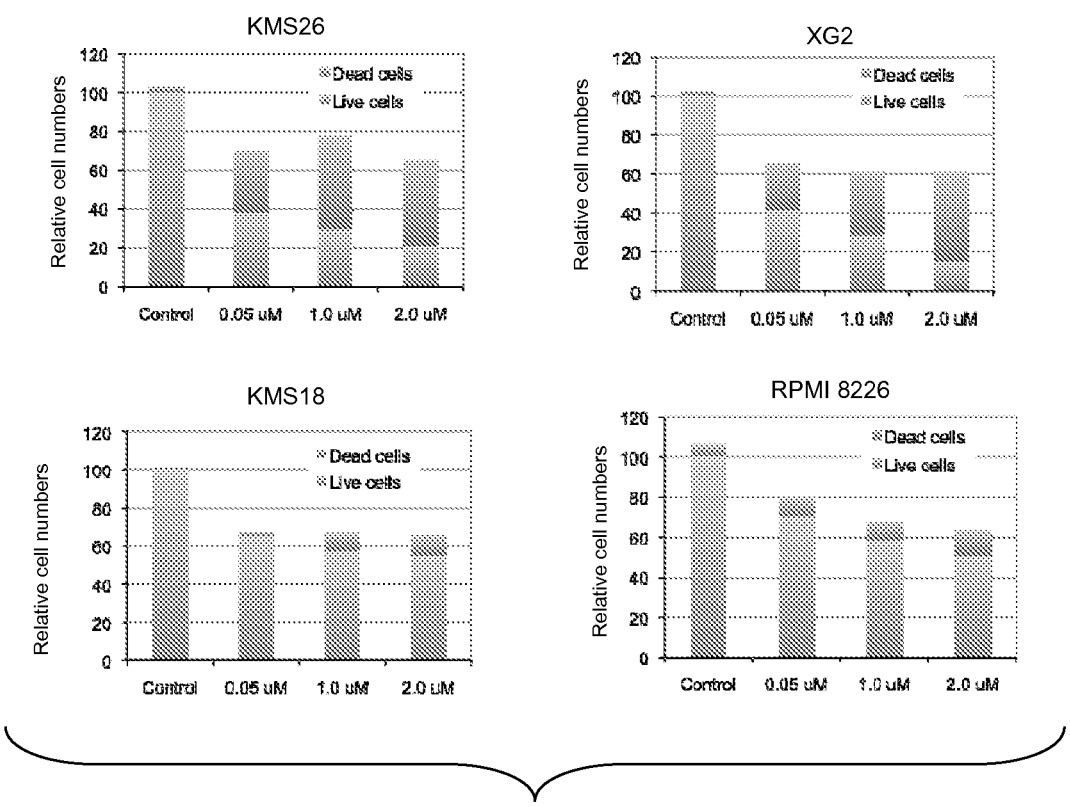
FIG. 15 shows that NSC697923 inhibits the growth of multiple myeloma cells. The indicated multiple myeloma cells were seeded at 300,000 cells/mL in 6-well plates and cultured in the presence of DMSO (0.2%, control) or various concentrations of NSC697923 for 24 hours. The live and dead cells were counted using the trypan blue exclusion assay. Shown are the means from 3 separate experiments. The average number of live cells in the control was set at 100.

It has been shown that multiple myeloma cells also depend on NF-kB signaling for survival. It was thus hypothesized that these cells may also sensitive to NSC697923 treatment. FIG. 15 shows that NSC697923 inhibits the growth of multiple myeloma cells. The indicated multiple myeloma cells were seeded at 300,000 cells/mL in 6-well plates and cultured in the presence of DMSO (0.2%, control) or various concentrations of NSC697923 for 24 hours. The live and dead cells were counted using the trypan blue exclusion assay. Shown are the means from 3 separate experiments. The average number of live cells in the control was set at 100.

Example 13

In Vivo Treatment of DLBCL Xenograft Model

Female CB.17 SCID mice (Taconic Farms) will be used for in vivo studies with OCI-Ly7 (GCB DLBCL) and OCI-Ly10 (ABC DLBCL). All animals will be housed and handled in accordance with the Guide for the Care and Use of Laboratory Animals. For subcutaneous xenograft studies, mice will be inoculated with $1 \times 10^7$ OCI-Ly7 or OCI-Ly10 cells with Matrigel (BD Biosciences) in the right flank, and tumor growth will be monitored with caliper measurements. When the mean tumor volume reaches approximately 200 $mm^3$, animals will dosed once daily for 7 days via intravenous administration with vehicle (10% cyclodextrin) or NSC697923 in saline at dosages of either 2.5 mg/kg, 12.5 mg/kg, and 25 mg/kg. Inhibition of tumor growth (T/C, average treated tumor volume/average control tumor volume) will be calculated one day following the last day of treatment. N=3 per group. It is expected that a dose-dependent response will be observed, with effective tumor shrinkage following NSC697923 administration.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of causing cell death of malignant B cells of diffuse large cell lymphoma comprising:

introducing a compound having a structure

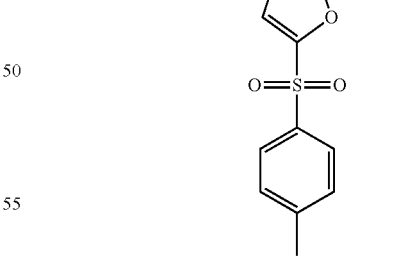

into a malignant B cell of diffuse large cell lymphoma under conditions effective to cause cell death of the malignant B cell.

2. The method according to claim 1, wherein the compound is present in a pharmaceutical composition that also comprises a pharmaceutically-acceptable carrier.

3. The method according to claim 1, wherein the malignant B cell is in vitro.

4. The method according to claim 1, wherein the malignant B cell is in vivo.

5. The method according to claim 1 further comprising:
exposing the cell to an additional therapeutic agent, wherein the additional therapeutic agent is a CHOP combination therapy.

* * * * *